United States Patent
Dority et al.

(10) Patent No.: US 8,431,413 B2
(45) Date of Patent: Apr. 30, 2013

(54) FLUID PROCESSING AND CONTROL

(75) Inventors: Douglas B. Dority, Mill Valley, CA (US); Ronald Chang, Redwood City, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 13/245,572

(22) Filed: Sep. 26, 2011

(65) Prior Publication Data

US 2012/0034705 A1 Feb. 9, 2012

Related U.S. Application Data

(62) Division of application No. 10/084,409, filed on Feb. 25, 2002, now Pat. No. 8,048,386.

(51) Int. Cl.
*G01N 33/53* (2006.01)

(52) U.S. Cl.
USPC ........ 436/500; 422/501; 436/180; 73/863.71; 73/863.72; 73/863.73; 210/222; 210/223

(58) Field of Classification Search .......... 422/500–501; 436/180; 73/863.71, 863.72, 863.73; 210/222–223
See application file for complete search history.

(56) References Cited

U.S. PATENT DOCUMENTS

| | | | |
|---|---|---|---|
| 3,616,453 A * | 10/1971 | Philpot | ........................ 204/647 |
| 3,645,142 A | 2/1972 | Turpin | |
| 4,068,528 A | 1/1978 | Gundelfinger | |
| 4,231,990 A | 11/1980 | Jottier | |
| 4,506,558 A | 3/1985 | Bakalyar | |
| 4,690,801 A | 9/1987 | Anderson et al. | |
| 4,702,889 A | 10/1987 | Cabrera et al. | |
| 4,705,059 A | 11/1987 | Lecerf et al. | |
| 4,726,237 A | 2/1988 | Yung | |
| 4,726,932 A | 2/1988 | Feier et al. | |
| 4,752,445 A | 6/1988 | Zell | |
| 4,937,048 A | 6/1990 | Sakai et al. | |
| 4,948,565 A | 8/1990 | Bemis et al. | |
| 4,983,523 A | 1/1991 | Li et al. | |

(Continued)

FOREIGN PATENT DOCUMENTS

| | | |
|---|---|---|
| EP | 0 481 285 A2 | 4/1992 |
| GB | 994 648 A | 6/1965 |

(Continued)

OTHER PUBLICATIONS

Supplementary European Search Report from EP 03711029 dated Sep. 17, 2010.

(Continued)

*Primary Examiner* — Jyoti Nagpaul

(57) ABSTRACT

A fluid control and processing system for controlling fluid flow among a plurality of chambers comprises a body including a fluid processing region continuously coupled fluidicly with a fluid displacement region. The fluid displacement region is depressurizable to draw fluid into the fluid displacement region and pressurizable to expel fluid from the fluid displacement region. The body includes at least one external port. The fluid processing region is fluidicly coupled with the at least one external port. The fluid displacement region is fluidicly coupled with at least one external port of the body. The body is adjustable with respect to the plurality of chambers to place the at least one external port selectively in fluidic communication with the plurality of chambers.

9 Claims, 42 Drawing Sheets

U.S. PATENT DOCUMENTS

| | | |
|---|---|---|
| 5,062,547 A | 11/1991 | Zähner et al. |
| 5,105,851 A | 4/1992 | Fogelman |
| 5,143,084 A | 9/1992 | Macemon et al. |
| 5,250,263 A | 10/1993 | Manz |
| 5,273,656 A | 12/1993 | Anderson et al. |
| 5,374,522 A | 12/1994 | Murphy et al. |
| 5,425,921 A | 6/1995 | Coakley et al. |
| 5,652,141 A | 7/1997 | Henco et al. |
| 5,731,212 A | 3/1998 | Gavin et al. |
| 5,856,174 A | 1/1999 | Lipshutz et al. |
| 5,882,903 A | 3/1999 | Andrevski et al. |
| 5,922,288 A | 7/1999 | Herst |
| 5,922,591 A | 7/1999 | Anderson et al. |
| 5,935,858 A | 8/1999 | Herst |
| 6,012,488 A | 1/2000 | Nichols |
| 6,043,080 A | 3/2000 | Lipshutz et al. |
| 6,100,084 A | 8/2000 | Miles et al. |
| 6,162,400 A | 12/2000 | Schembri |
| 6,168,948 B1 | 1/2001 | Anderson et al. |
| 6,374,684 B1 | 4/2002 | Dority |
| 6,387,710 B1 | 5/2002 | Loewy et al. |
| 6,818,185 B1 | 11/2004 | Peterson et al. |
| 2002/0131905 A1 | 9/2002 | Cordill |
| 2003/0072679 A1 | 4/2003 | Johnson et al. |

FOREIGN PATENT DOCUMENTS

| | | |
|---|---|---|
| JP | 59-214769 A | 12/1984 |
| JP | 61-501873 A | 8/1986 |
| JP | 62-002124 A | 1/1987 |
| JP | 1-12210 Y2 | 4/1989 |
| JP | 03-041320 A | 2/1991 |
| JP | 04-307349 A | 10/1992 |
| JP | 5-5474 Y2 | 2/1993 |
| JP | 05-118452 A | 5/1993 |
| JP | 05-333022 A | 12/1993 |
| JP | 06-213778 A | 8/1994 |
| JP | 09-033537 A | 2/1997 |
| JP | 09-171025 A | 6/1997 |
| JP | 09-229929 A | 9/1997 |
| JP | 2000-241416 | 9/2000 |
| WO | WO 85/04719 A1 | 10/1985 |
| WO | WO 93/10432 A1 | 5/1993 |
| WO | WO 97/16561 A1 | 5/1997 |
| WO | WO 99/28038 A1 | 6/1999 |
| WO | WO 99/33559 A1 | 8/1999 |
| WO | WO 99/47255 A1 | 9/1999 |
| WO | WO 00/72970 A1 | 12/2000 |
| WO | WO 00/73412 A2 | 12/2000 |
| WO | WO 00/73413 A2 | 12/2000 |
| WO | WO 00/73413 A3 | 12/2000 |
| WO | WO 02/18902 A1 | 3/2002 |

OTHER PUBLICATIONS

English Translation of Japanese Laid-Open Publication No. 2000-241416, published Sep. 8, 2000 and filed by Applicant Toto Instrument Corp. on Feb. 23, 1999.

* cited by examiner

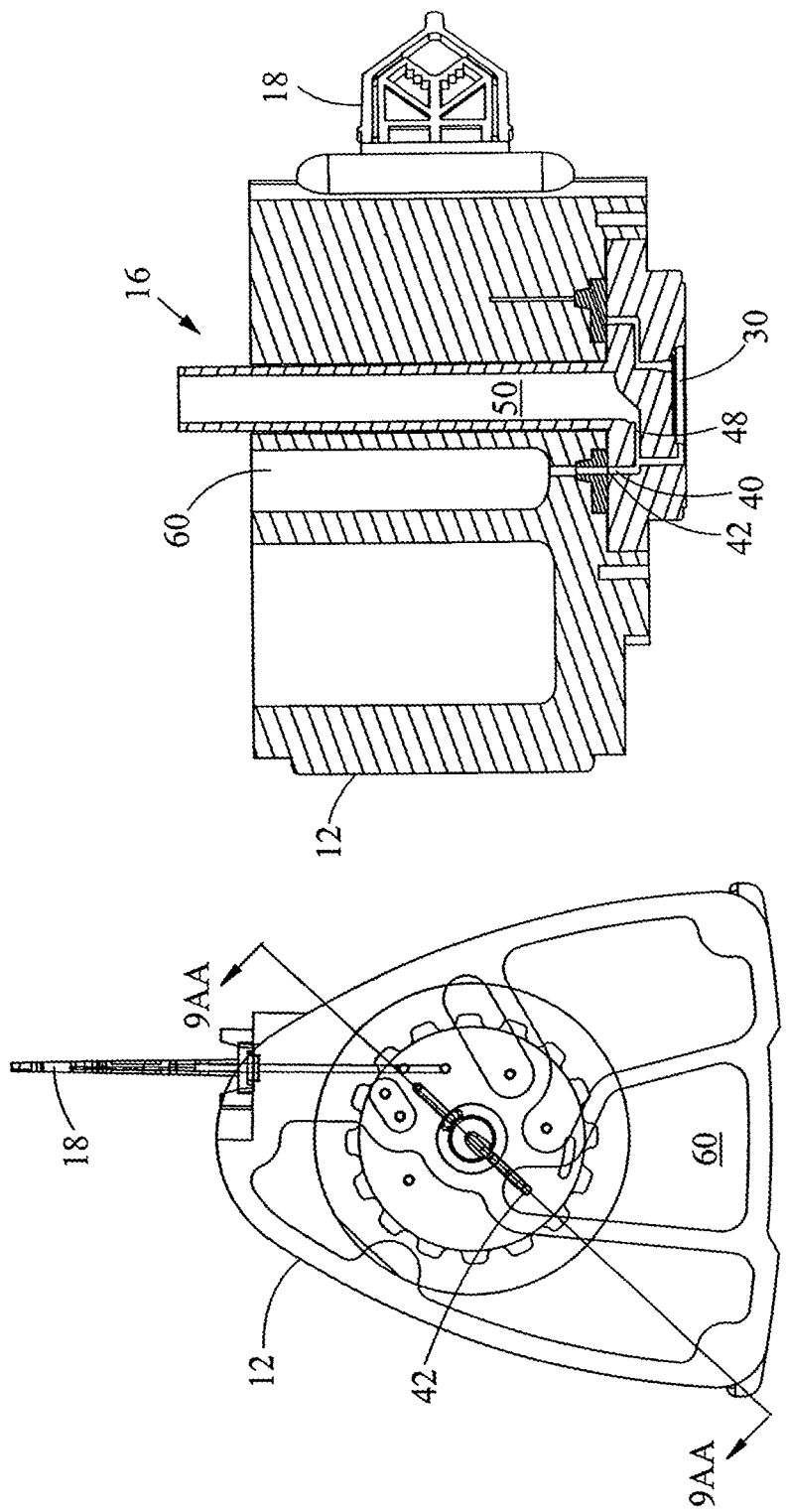

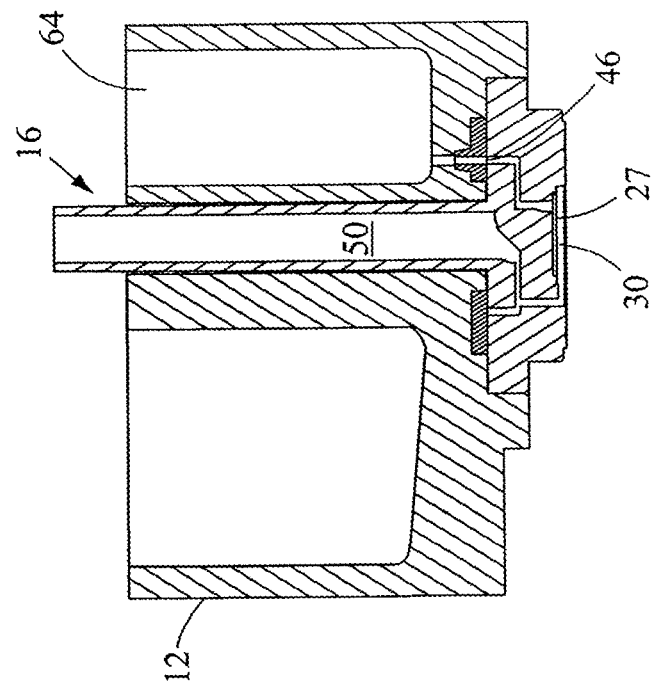
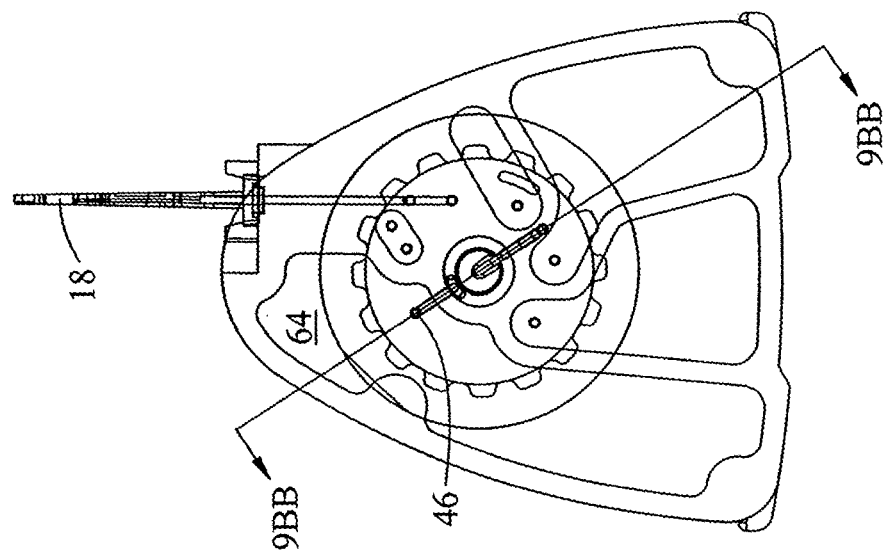
FIG. 9B
FIG. 9BB

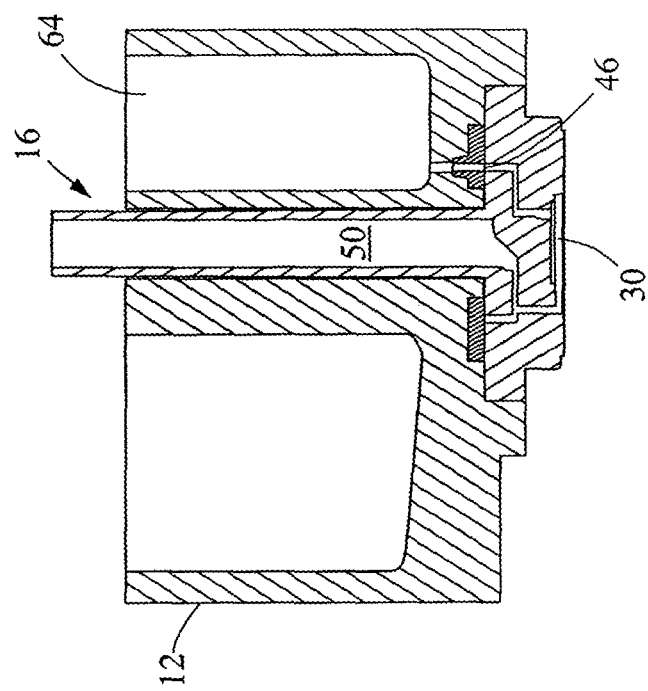
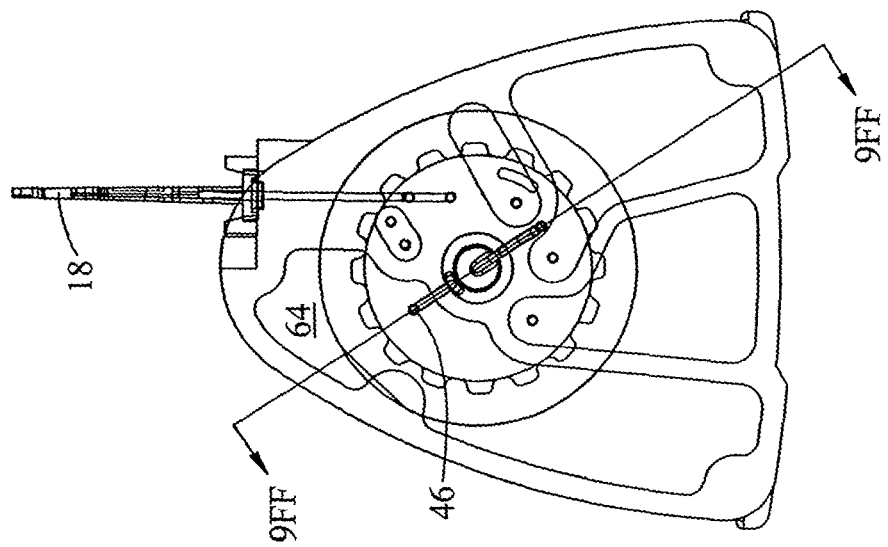
FIG. 9FF
FIG. 9F

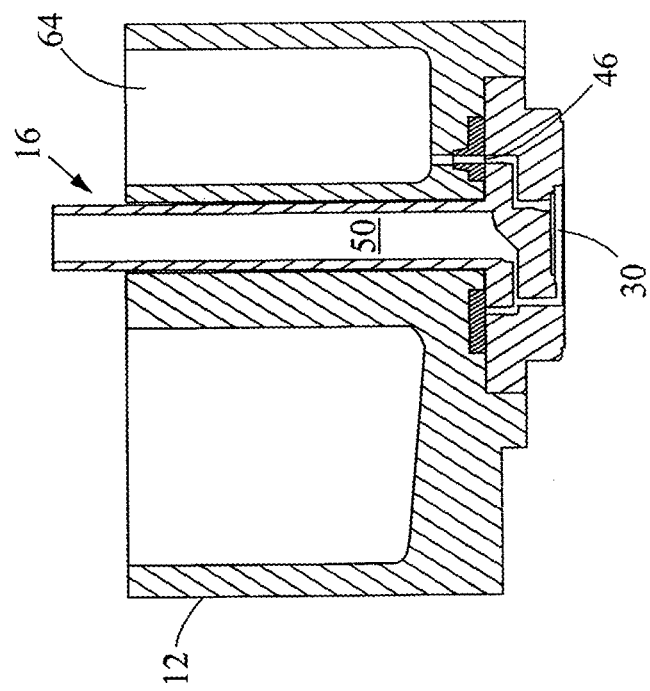
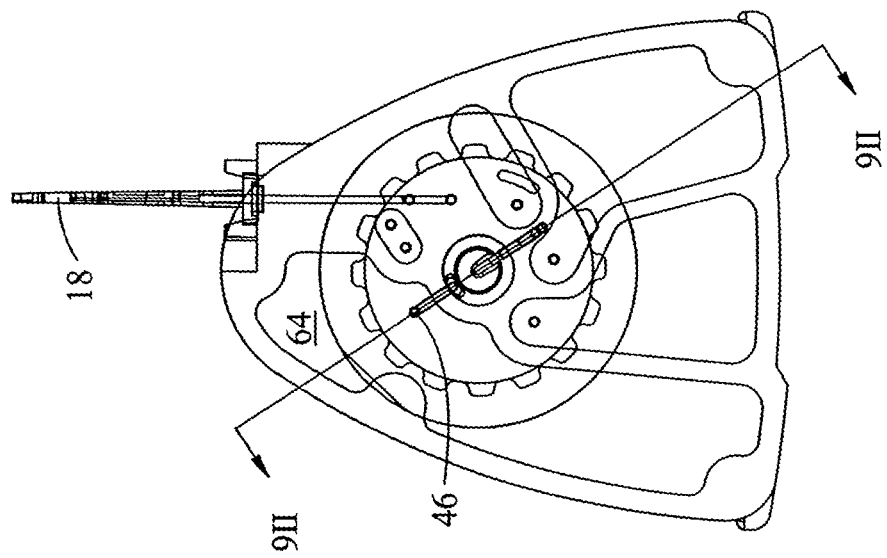
FIG. 9II
FIG. 9I

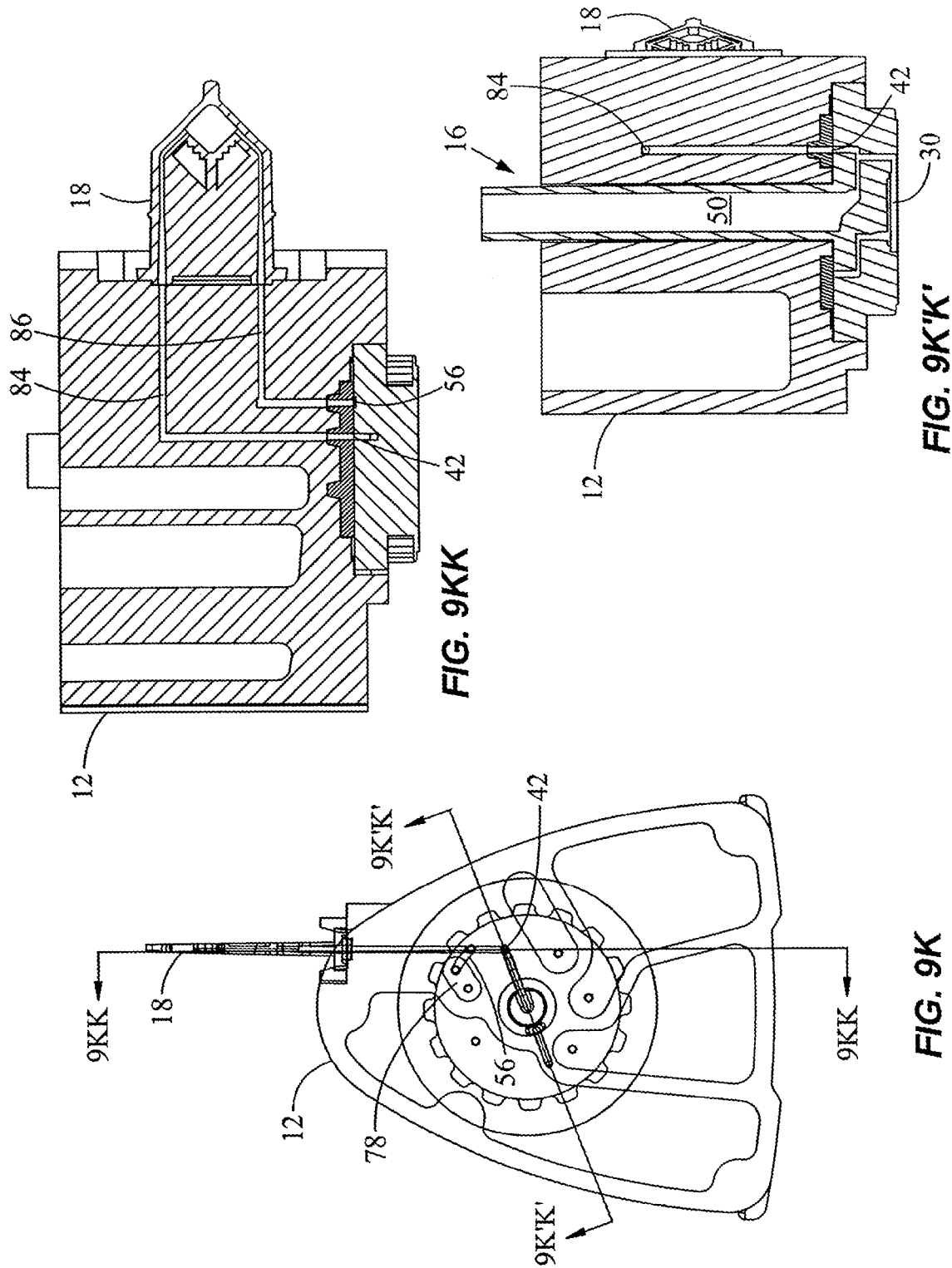

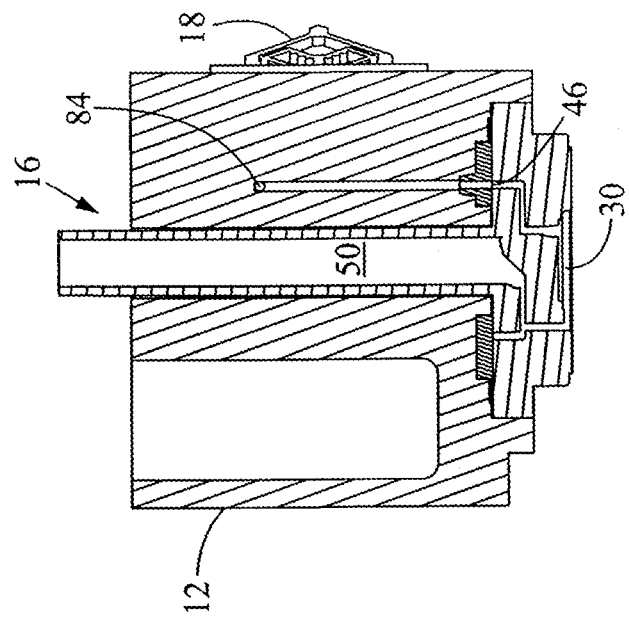
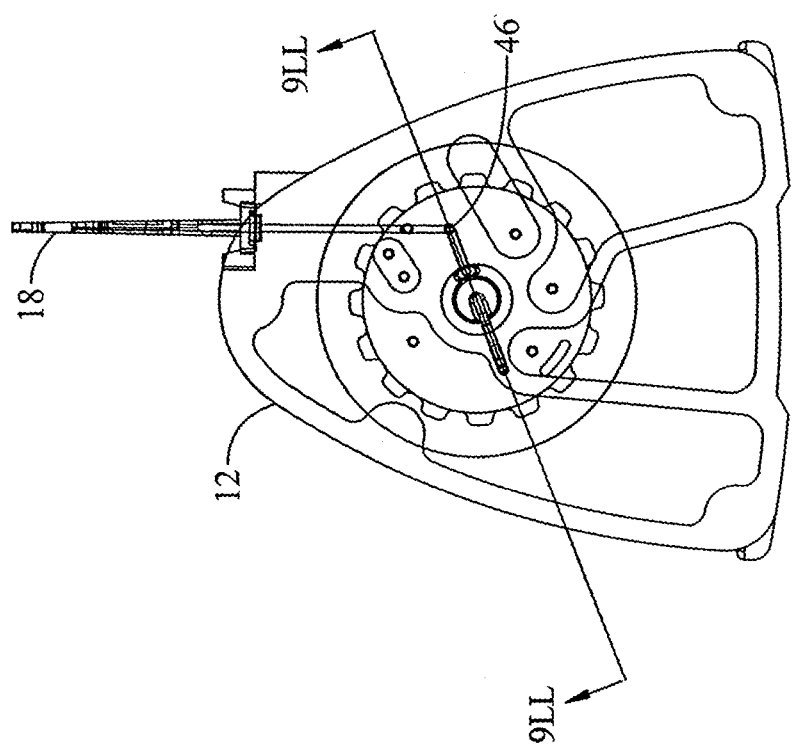
FIG. 9LL
FIG. 9L

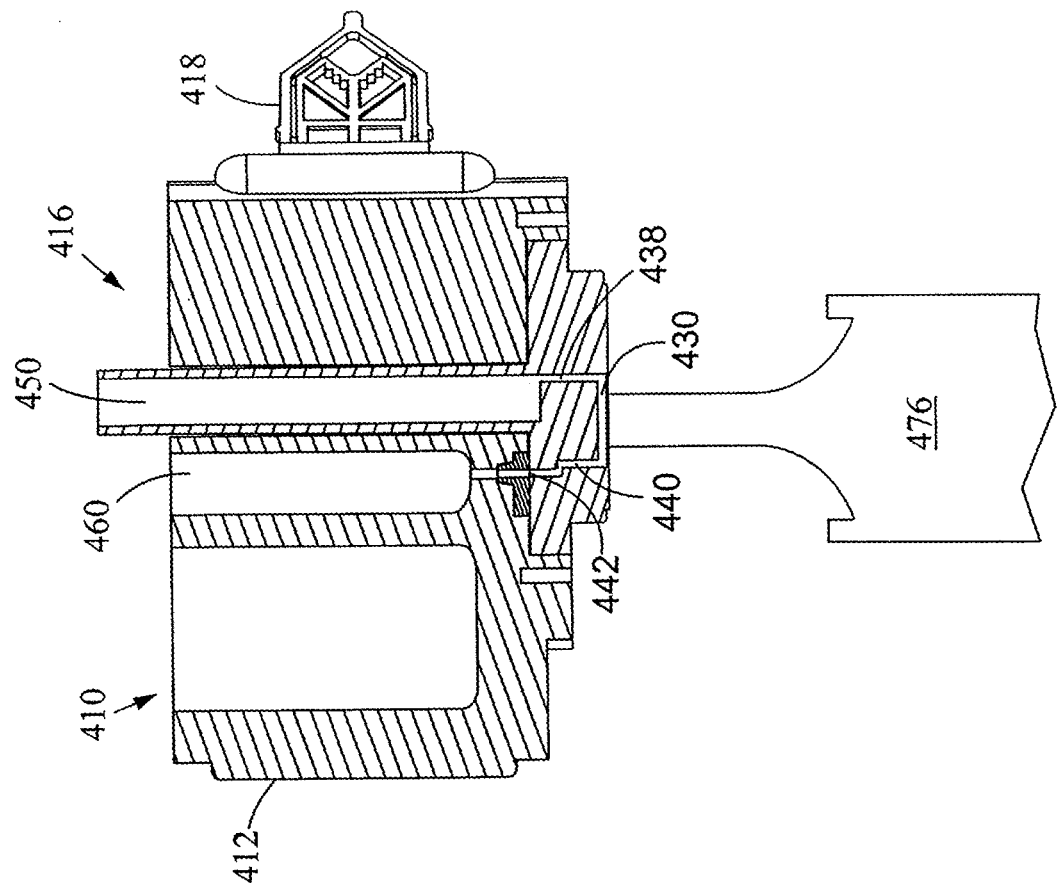
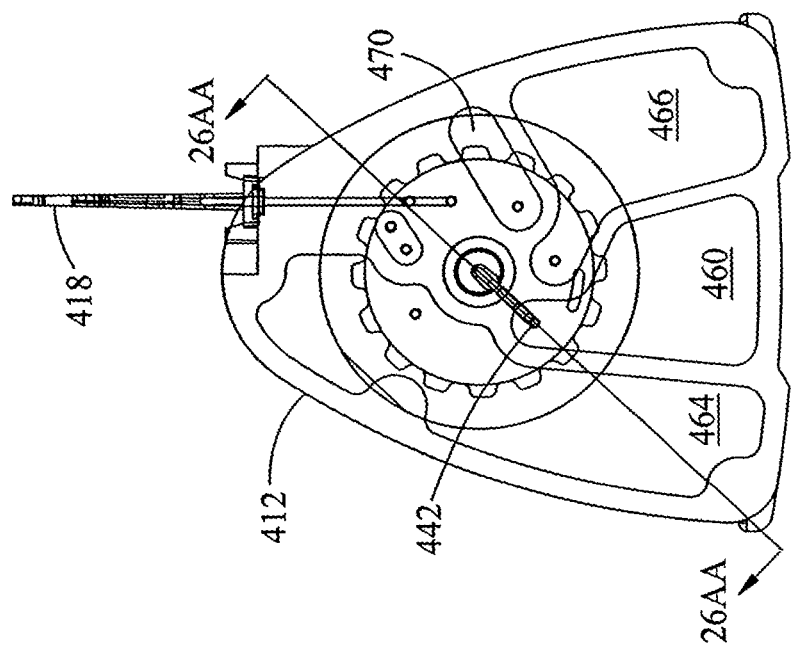
FIG. 26AA
FIG. 26A

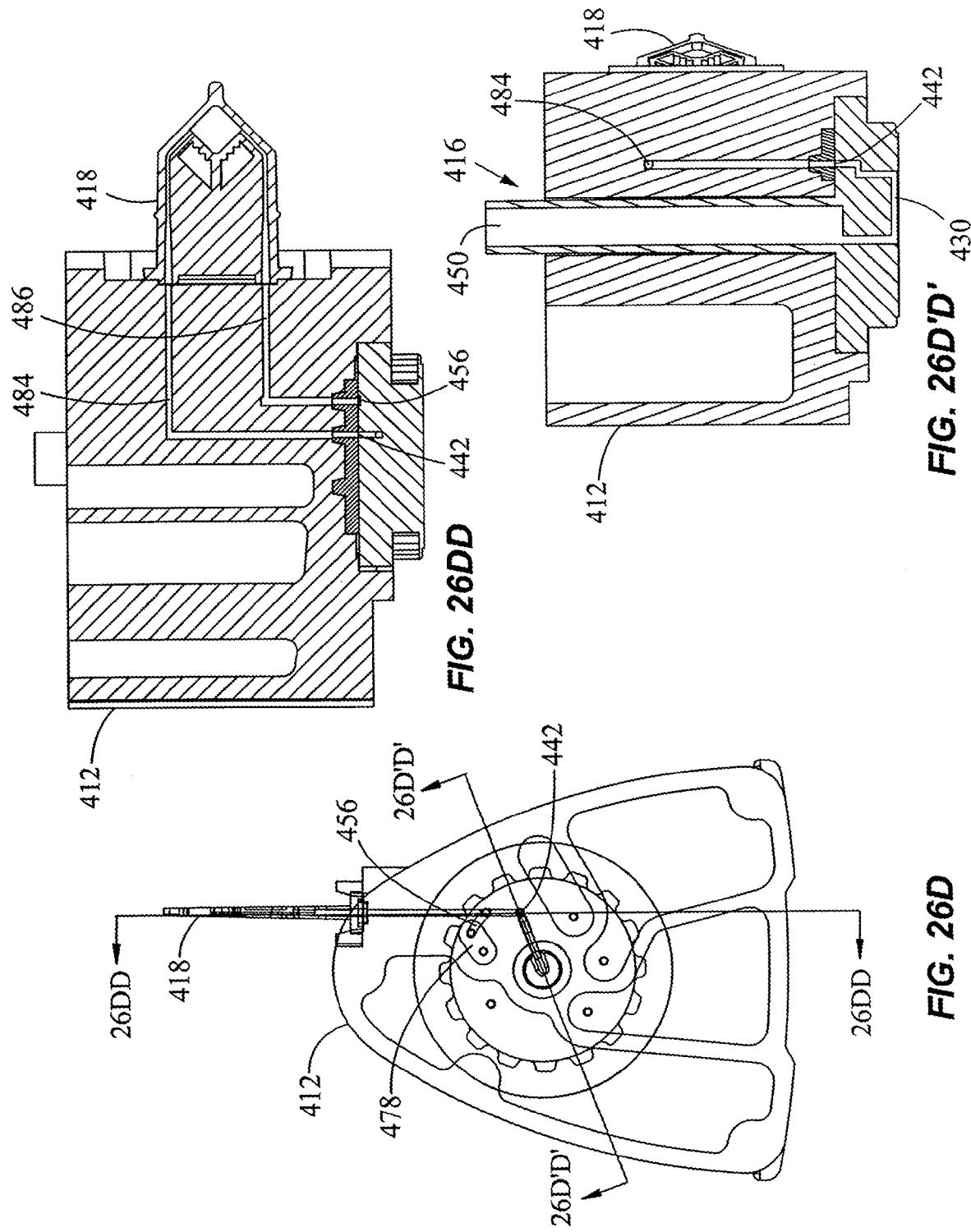

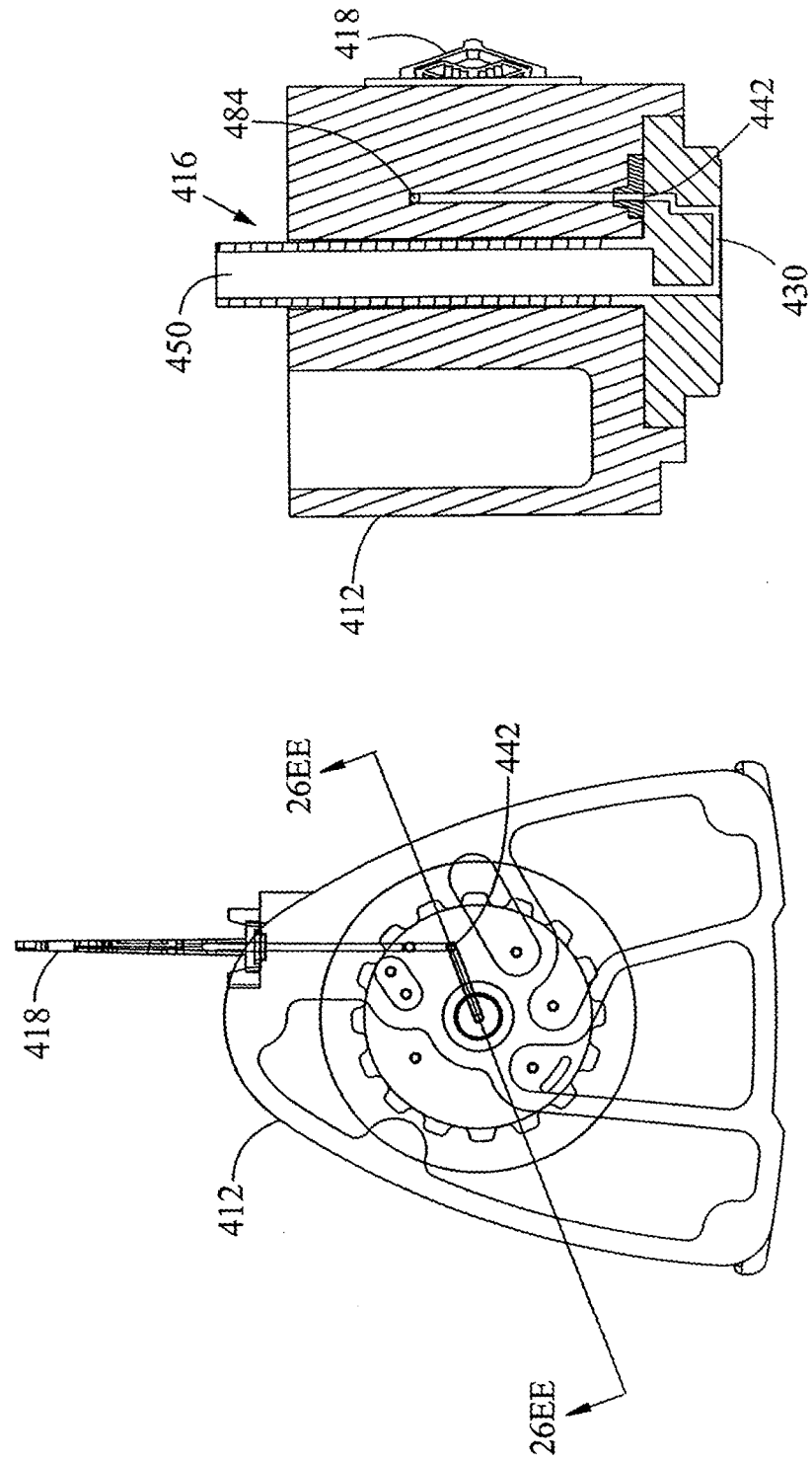

FLUID PROCESSING AND CONTROL

CROSS-REFERENCES TO RELATED APPLICATIONS

This application is a division of U.S. patent application Ser. No. 10/084,409, filed Feb. 25, 2002, the contents of which are incorporated by reference in the entirety. Also incorporated by reference in the entirety are the contents of a related, commonly assigned U.S. patent application Ser. No. 09/648,570, now U.S. Pat. No. 6,374,684.

BACKGROUND OF THE INVENTION

The present invention relates generally to fluid manipulation and, more particularly, to a system and method for metering and distributing fluid for processing and analysis.

The analysis of fluids such as clinical or environmental fluids generally involves a series of processing steps, which may include chemical, optical, electrical, mechanical, thermal, or acoustical processing of the fluid samples. Whether incorporated into a bench-top instrument, a disposable cartridge, or a combination of the two, such processing typically involves complex fluidic assemblies and processing algorithms.

Conventional systems for processing fluid samples employ a series of chambers each configured for subjecting the fluid sample to a specific processing step. As the fluid sample flows through the system sequentially from chamber to chamber, the fluid sample undergoes the processing steps according to a specific protocol. Because different protocols require different configurations, conventional systems employing such sequential processing arrangements are not versatile or easily adaptable to different protocols.

SUMMARY OF THE INVENTION

The present invention provides an apparatus and method for manipulating fluids, for instance, to determine the presence or absence of an analyte in a sample. In a specific embodiment, the apparatus employs a rotary valve configuration that allows fluidic communication between a fluid processing region selectively with a plurality of chambers including, for example, a sample chamber, a waste chamber, a wash chamber, a lysis chamber, and a mastermix or reagent chamber. The fluid flow among the fluid processing region and the chambers is controlled by adjusting the position of the rotary valve. In this way, the metering and distribution of fluids in the apparatus can be varied depending on the specific protocol. Unlike conventional devices, the fluid flow is no longer limited to a specific protocol.

In accordance with an aspect of the present invention, a fluid control and processing system comprises a housing having a plurality of chambers, and a valve body including a first fluid processing region continuously coupled fluidicly with a fluid displacement region. The fluid displacement region is depressurizable to draw fluid into the fluid displacement region and pressurizable to expel fluid from the fluid displacement region. The valve body includes a plurality of external ports. The first fluid processing region is fluidicly coupled with at least two of the external ports. The fluid displacement region is fluidicly coupled with at least one of the external ports of the valve body. The valve body is adjustable with respect to the housing to allow the external ports to be placed selectively in fluidic communication with the plurality of chambers. At least one of the plurality of chambers is a processing chamber including a first port and a second port for selectively communicating with at least one of the external ports of the valve body. The processing chamber provides an additional fluid processing region.

In some embodiments, at least one of the fluid processing regions in the valve body or in the processing chamber contains a fluid processing material which is an enrichment material or a depletion material. The fluid processing material may comprise at least one solid phase material. The solid phase material may comprise at least one of beads, fibers, membranes, filter paper, glass wool, polymers, and gels. The fluid processing material may comprise a filter and beads, or at least two types of beads. In a specific embodiments, a single type of beads is used to perform at least two different functions which are selected from the group consisting of cell capture, cell lysis, binding of analyte, and binding of unwanted material. In some embodiments, the processing chamber includes a receiving area for receiving a processing module containing an enrichment material or a depletion material. In a specific embodiment, at least one of the chambers is a reagent chamber containing dried or lyophilized reagents.

In some embodiments, the fluid processing material comprises at least one liquid phase material, such as ficoll, dextran, polyethylene glycol, and sucrose. The fluid processing material is contained in the fluid processing region by one or more frits. In a specific embodiment, the external ports are disposed on a generally planar external port surface of the valve body.

In accordance with another aspect of the invention, a fluid control and processing system comprises a housing having a plurality of chambers and at least one separation channel (e.g., for performing capillary electrophoresis or isoelectric focusing), and a valve body including a fluid processing region continuously coupled fluidicly with a fluid displacement region. The fluid displacement region is depressurizable to draw fluid into the fluid displacement region and pressurizable to expel fluid from the fluid displacement region. The valve body includes at least one external port, the fluid processing region is fluidicly coupled with the at least one external port, and the fluid displacement region is fluidicly coupled with at least one external port of the valve body. The valve body is adjustable with respect to the housing to allow the at least one external port to be placed selectively in fluidic communication with the plurality of chambers and with the at least one separation channel.

In some embodiments, a plurality of electrodes are coupled to the housing to apply an electric field across at least a portion of the separation channel. The electrodes preferably comprise a pair of metal tubes at the two opposite ends of the separation channel. Reservoirs are provided at both ends of the separation channel, and a reservoir port is provided at one of the reservoirs for communicating with the at least one external port of the valve body.

Another aspect of the present invention is directed to a method for controlling fluid flow between a valve, a plurality of chambers, and at least one separation channel, wherein the valve includes at least one external port and a fluid displacement region continuously coupled fluidicly with a fluid processing region which is fluidicly coupled with the at least one external port. The method comprises adjusting the valve with respect to the plurality of chambers and the at least one separation channel to place the at least one external port selectively in fluidic communication with the plurality of chambers and the at least one separation channel.

In some embodiments, an electric field is applied across at least a portion of the separation channel. The method may comprise optically detecting species bands in the separation channel.

In accordance with another aspect of the invention, a fluid control and processing system comprises a housing having a plurality of chambers, and a valve body including a fluid processing region continuously coupled fluidicly with a fluid displacement region. The fluid displacement region is depressurizable to draw fluid into the fluid displacement region and pressurizable to expel fluid from the fluid displacement region. The valve body includes an external port. The fluid processing region is fluidicly coupled with the external port. The fluid displacement region is fluidicly coupled with the external port of the valve body. The valve body is adjustable with respect to the housing to allow the external port to be placed selectively in fluidic communication with the plurality of chambers.

In some embodiments, the valve body is adjustable with respect to the housing to close the external port so that the fluid displacement region and the fluid processing region are fluidicly isolated from the chambers. At least one of the chambers and the fluid processing region may contain an enrichment material or a depletion material. The fluid displacement region is depressurizable by increasing in volume and is pressurizable by decreasing in volume. A fluid displacement member is disposed in the fluid displacement region, and is movable to adjust the volume of the fluid displacement region. An energy transmitting member is operatively coupled with the fluid processing region for transmitting energy thereto to process fluid contained therein.

In specific embodiments, the valve body includes a crossover channel. The valve body is adjustable with respect to the housing to place the crossover channel in fluidic communication with an aspiration chamber and a source chamber to permit aspiration of a fluid from the source chamber through the crossover channel to the aspiration chamber. The body is rotatably adjustable around an axis. The at least one external port is disposed within a range of external port radii from the axis and the crossover channel is disposed within a range of crossover channel radii from the axis. The range of external port radii and the range of crossover channel radii are non-overlapping. The crossover channel may be a circular arc lying on a common crossover channel radius from the axis.

In accordance with another aspect of the present invention, a fluid control and processing system for controlling fluid flow among a plurality of chambers comprises a body including a fluid processing region continuously coupled fluidicly with a fluid displacement region. The fluid displacement region is depressurizable to draw fluid into the fluid displacement region and pressurizable to expel fluid from the fluid displacement region, the body including at least one external port. The fluid processing region is fluidicly coupled with the at least one external port. The fluid displacement region is fluidicly coupled with at least one external port of the valve body. The body is rotatably adjustable and relative to the plurality of chambers to place the at least one external port selectively in fluidic communication with the plurality of chambers.

BRIEF DESCRIPTION OF THE DRAWINGS

FIGS. 9A-9LL are top plan views and cross-sectional views illustrating a specific protocol for controlling and processing fluid using the fluid control and processing system of FIG. 1;

FIGS. 26A-26EE are top plan views and cross-sectional views illustrating a specific protocol for controlling and processing fluid using the fluid control and processing system of FIG. 25.

DESCRIPTION OF THE SPECIFIC EMBODIMENTS

Figure 1:
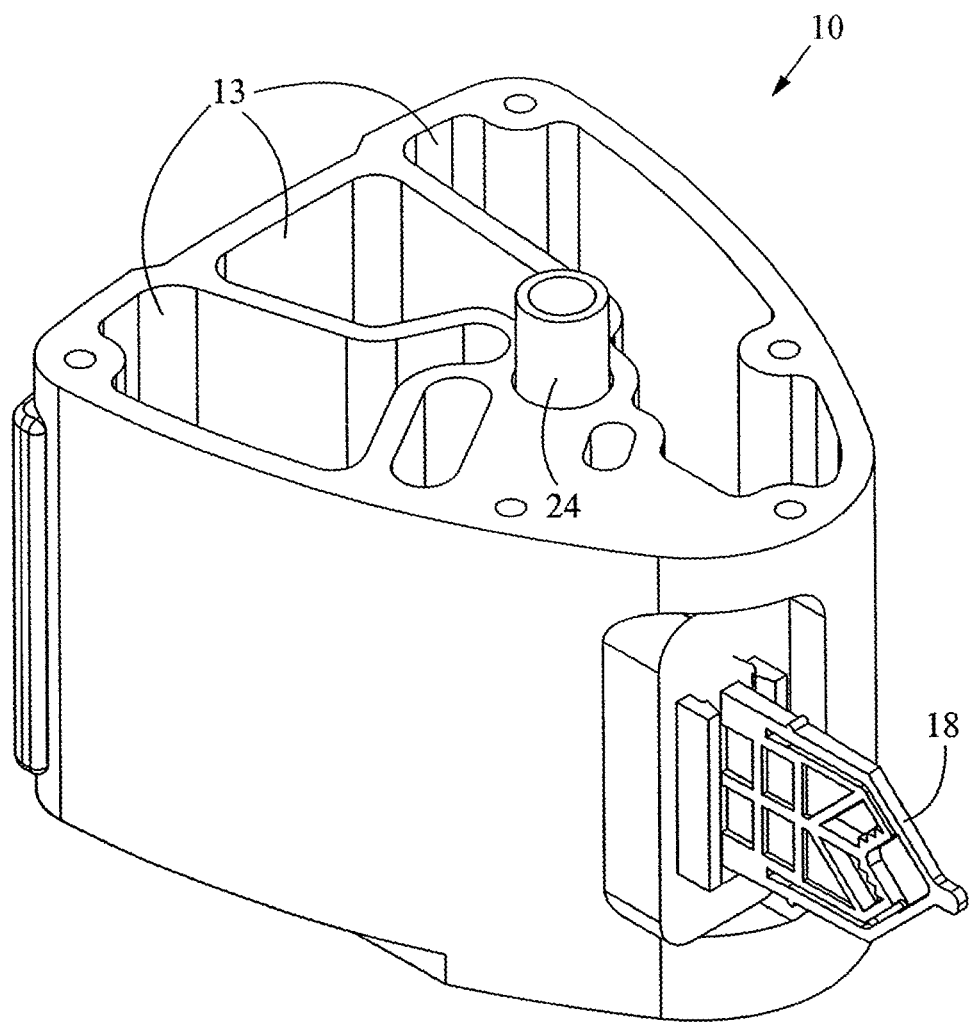
FIG. 1 is a perspective view of the fluid control and processing system according to an embodiment of the present invention.
Figure 2:
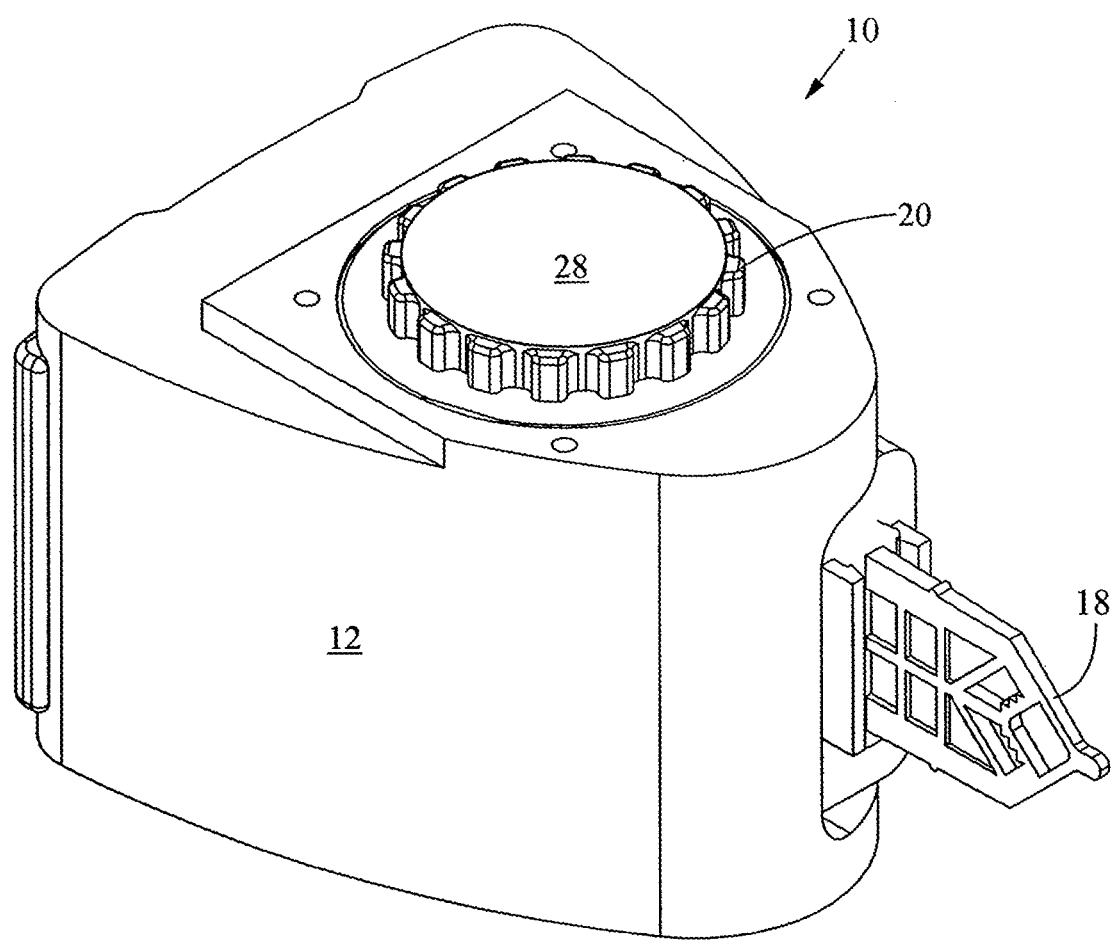
FIG. 2 is another perspective view of the system of FIG. 1.
Figure 3:
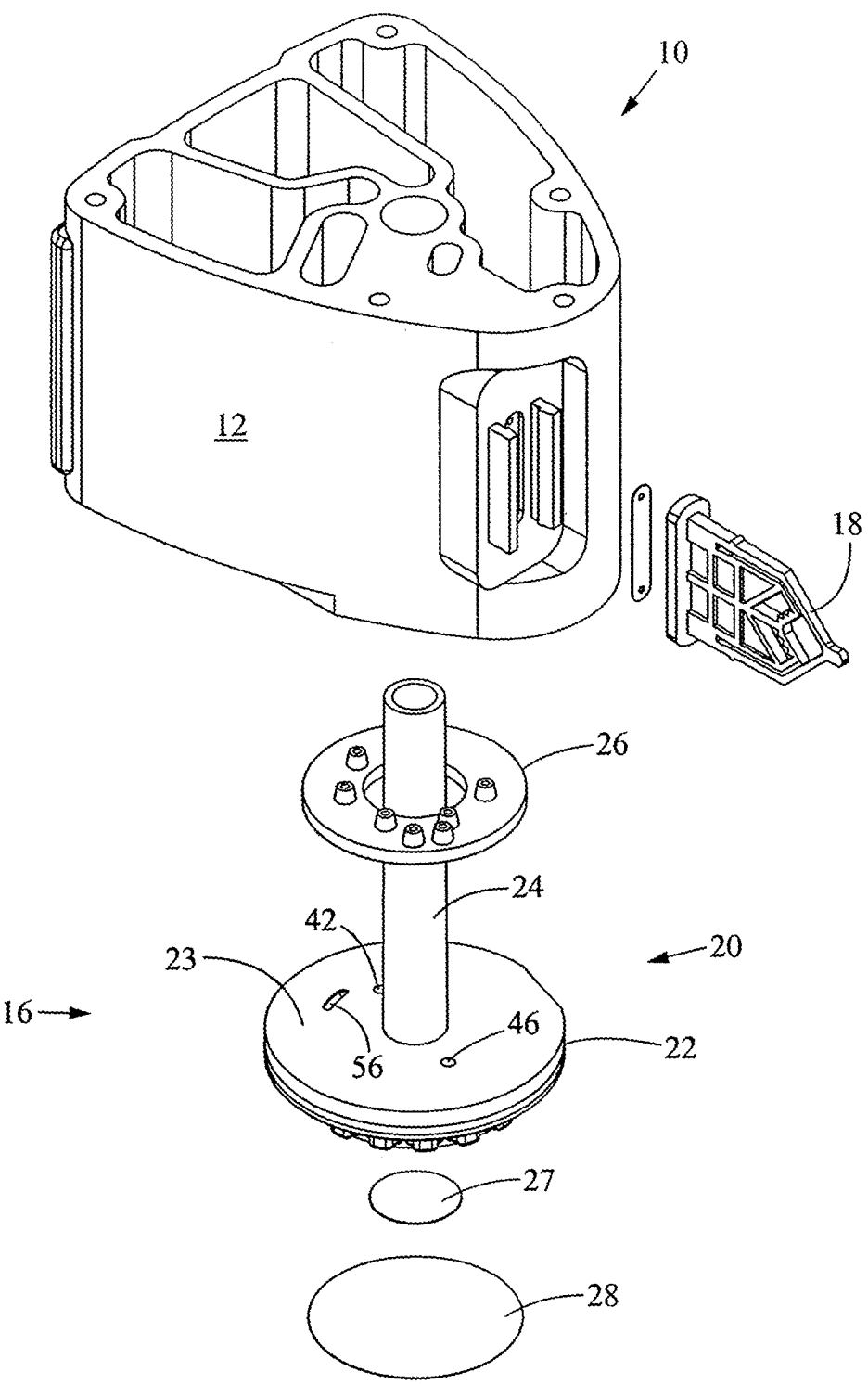
FIG. 3 is an exploded view of the system of FIG. 1.
Figure 4:
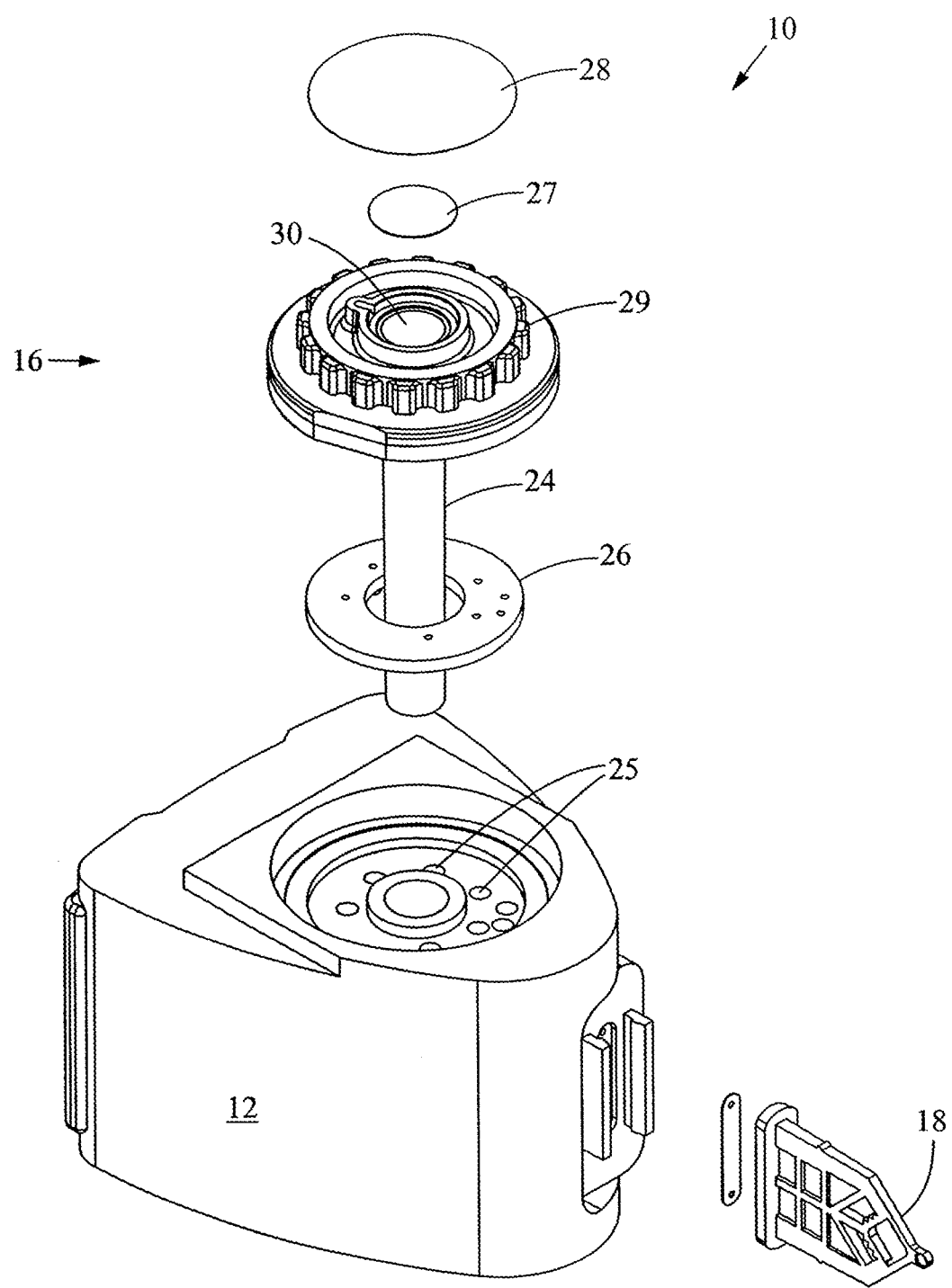
FIG. 4 is an exploded view of the system of FIG. 2.
Figure 5:
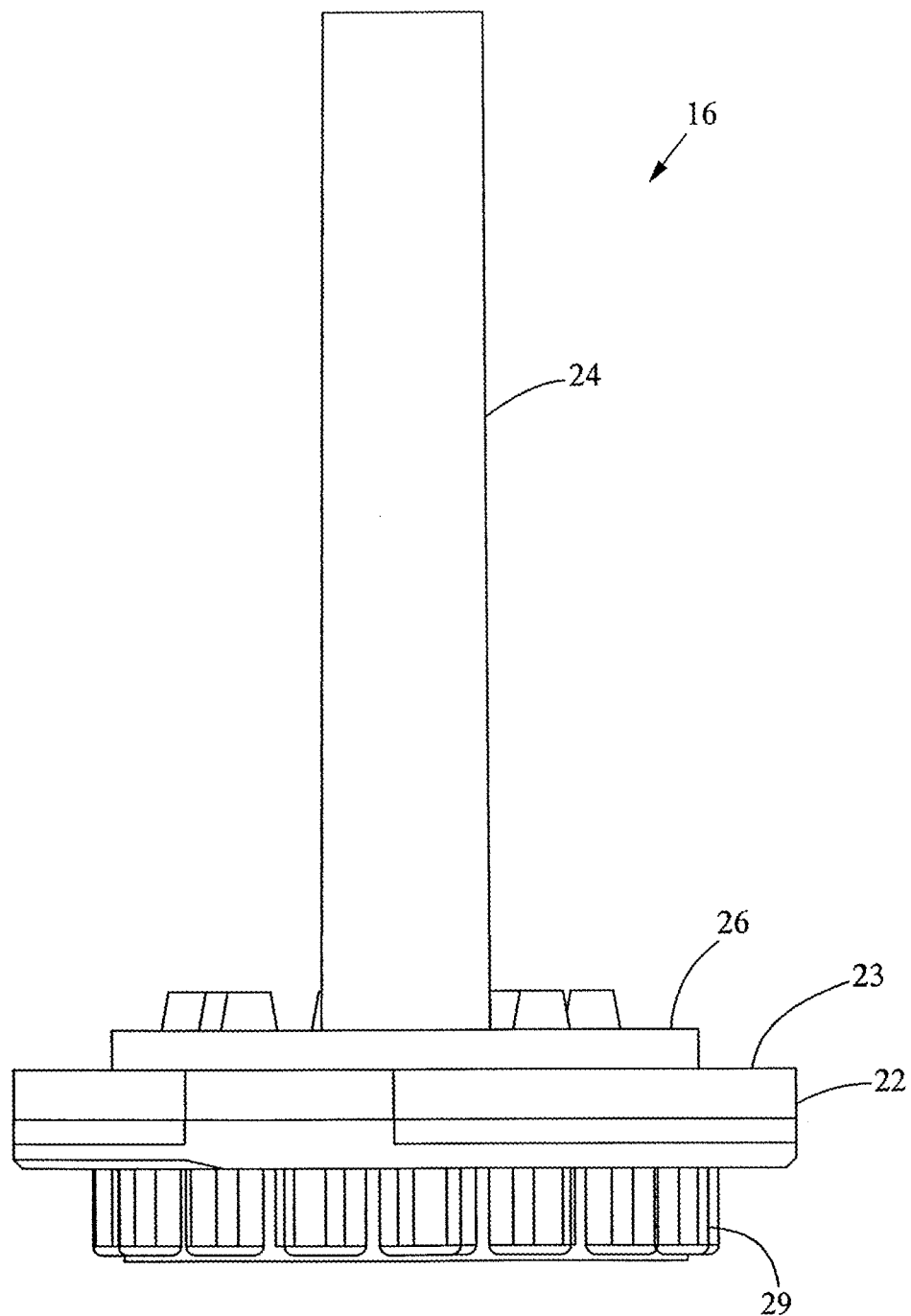
FIG. 5 is an elevational view of a fluid control apparatus and gasket in the system of FIG. 1.

FIGS. 1-4 show a fluid control and processing system 10 including a housing 12 having a plurality of chambers 13. FIG. 1 shows the chambers 13 exposed for illustrative purposes. A top cover will typically be provided to enclose the chambers 13. As best seen in FIGS. 3 and 4, a fluid control device 16 and a reaction vessel 18 are connected to different portions of the housing 12. The fluid control device in the embodiment shown is a rotary fluid control valve 16. The valve 16 includes a valve body 20 having a disk portion 22 and a tubular portion 24. The disk portion 22 has a generally planar external port surface 23, as best seen in FIG. 3. The valve 16 is rotatable relative to the housing 12. The housing 12 includes a plurality of chamber ports 25 facing the external port surface 23 of the disk portion 22 of the valve 16 (FIG. 4) to permit fluidic communication between the chambers 13 and the valve 16. An optional seal or gasket 26 is disposed between the disk portion 22 and the housing 12. The disk portion 22 further includes a filter or a filter stack 27 and an outer cover 28, and a toothed periphery 29. The cover 28 may be a rigid shell or a flexible film.

As best seen in FIG. 4, the disk portion 22 includes a fluid processing region 30. As used herein, the term "fluid processing region" refers to a region in which a fluid is subject to processing including, without limitation, chemical, optical, electrical, mechanical, thermal, or acoustical processing. For example, chemical processing may include a catalyst; optical processing may include U.V. activation; electrical processing may include electroporation or electrophoresis or isoelectric focusing; mechanical processing may include mixing, filtering, pressurization, and cell disruption; thermal processing may include heating or cooling; and acoustical processing may include the use of ultrasound. The fluid processing region may include an active member, such as the filter 27, to facilitate processing of the fluid. Examples of active members include a microfluidic chip, a solid phase material, a filter or a filter stack, an affinity matrix, a magnetic separation matrix, a size exclusion column, a capillary tube, or the like. Suitable solid phase materials include, without limitation, beads, fibers, membranes, filter paper, lysis paper impregnated with a lysing agent, glass wool, polymers, or gels. In a specific embodiment, the fluid processing region is used to prepare a sample for further processing, for instance, in the reaction vessel 18.

Figure 6:
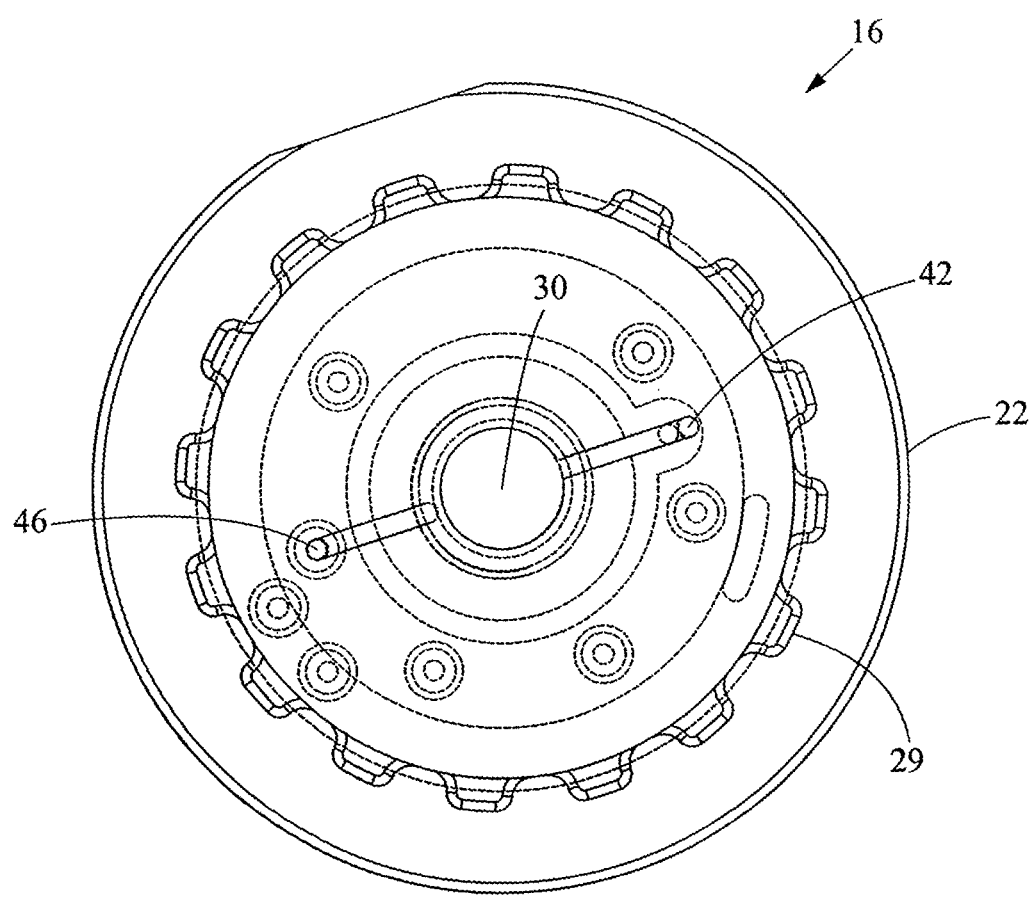
FIG. 6 is a bottom plan view of the fluid control apparatus and gasket of FIG. 5.
Figure 7:
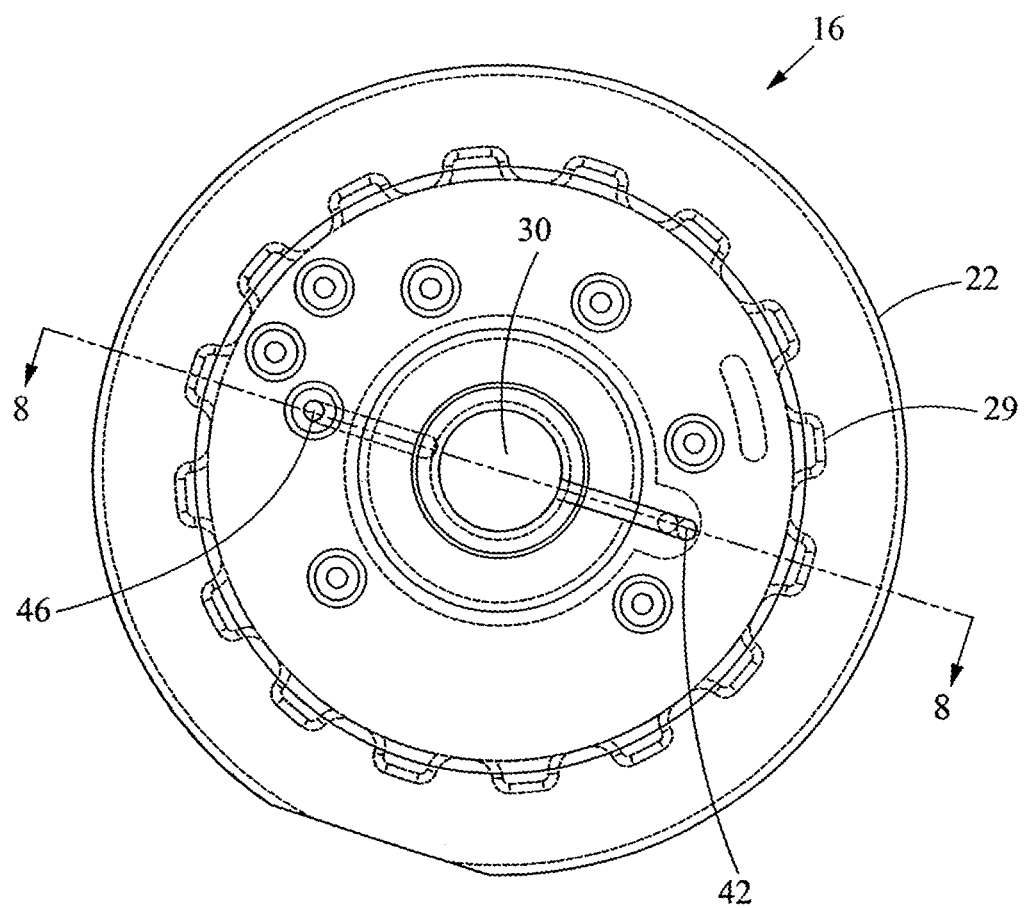
FIG. 7 is a top plan view of the fluid control apparatus and gasket of FIG. 5.
Figure 8:
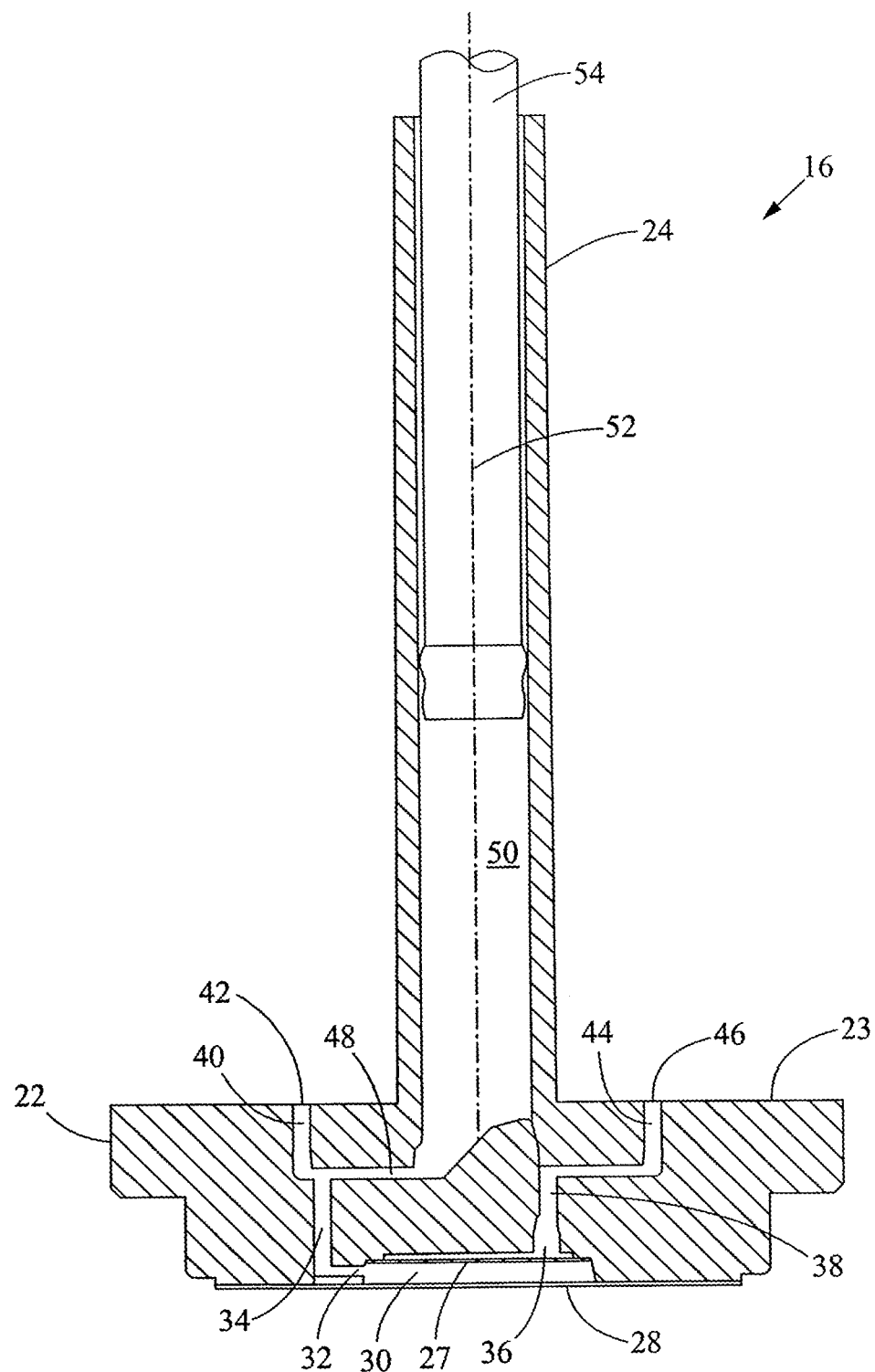
FIG. 8 is a cross-sectional view of the rotary fluid control apparatus of FIG. 7 along 8-8.

As shown in FIGS. 5-8, the outer cover 28 encloses the fluid processing region 30 and the bottom end of the disk portion 22 of the valve 16. In FIG. 8, the processing region 30 includes a first fluid processing port 32 coupled to a first fluid processing channel 34, and a second fluid processing port 36 coupled to a second fluid processing channel 38. The first fluid processing channel 34 is coupled to a first outer conduit 40 ending at a first external port 42 at the external port surface 23, while the second fluid processing channel 38 is coupled to a second outer conduit 44 ending at a second external port 46 at the external port surface 23. A fluid displacement channel 48 is coupled to the first fluid processing channel 34 and first conduit 40 near one end, and to a fluid displacement region 50 at the other end. The first outer conduit 40 serves as a common conduit for allowing fluidic communication between the first external port 42 and either or both of the first fluid processing channel 34 and the fluid displacement channel 48. The processing region 30 is in continuous fluidic communication with the fluid displacement region 50.

As shown in FIGS. 6-8, the external ports 42, 46 are angularly spaced from one another relative to the axis 52 of the valve 16 by about 180°. The external ports 42, 46 are spaced radially by the same distance from the axis 52. The axis 52 is perpendicular to the external port surface 23. In another embodiment, the angular spacing between the external ports 42, 46 may be different. The configuration of the channels in the disk portion 22 may also be different in another embodiment. For example, the first fluid processing channel 34 and the first outer conduit 40 may be slanted and coupled directly with the fluid displacement region 50, thereby eliminating the fluid displacement channel 48. The second fluid displacement channel 38 may also be slanted and extend between the second fluid processing port 36 and the second external port 46 via a straight line, thereby eliminating the second outer conduit 44. In addition, more channels and external ports may be provided in the valve 16. As best seen in FIG. 3, a crossover channel or groove 56 is desirably provided on the external port surface 23. The groove 56 is curved and desirably is spaced from the axis 52 by a constant radius. In one embodiment, the groove 56 is a circular arc lying on a common radius from the axis 52. As discussed in more detail below, the groove 56 is used for filling the vessel.

As shown in FIG. 8, the fluid displacement region 50 is disposed substantially within the tubular portion 24 of the valve 16 and extends partially into the disk portion 22. In a preferred embodiment, the fluid displacement region 50 is a pumping channel or chamber. A fluid displacement member in the form of a plunger or piston 54 is movably disposed in the pumping chamber 50. When the piston 54 moves upward, it expands the volume of the pumping chamber 50 to produce a suction for drawing fluid into the pumping chamber 50. When the piston 54 moves downward, it decreases the volume of the pumping chamber 50 to drive fluid out of the chamber 50. Alternatively, for example, pressurization and depressurization of the displacement region 50 may be carried out using a diaphragm, an external pneumatic or pressure control system, or the like.

As the rotary valve 16 is rotated around its axis 52 relative to the housing 12 of FIGS. 1-4, one of the external ports 42, 46 may be open and fluidicly coupled with one of the chambers 13 or reaction vessel 18, or both external ports 42, 46 may be blocked or closed. In this embodiment, at most only one of the external ports 42, 46 is fluidicly coupled with one of the chambers or reaction vessel 18. Other embodiments may be configured to permit both external ports 42, 46 to be fluidicly coupled with separate chambers or the reaction vessel 18. Thus, the valve 16 is rotatable with respect to the housing 12 to allow the external ports 42, 46 to be placed selectively in fluidic communication with a plurality of chambers which include the chambers 13 and the reaction vessel 18. Depending on which external port 42, 46 is opened or closed and whether the piston 54 is moved upward or downward, the fluid flow in the valve 16 can change directions, the external ports 42, 46 can each switch from being an inlet port to an outlet port, and the fluid flow may pass through the processing region 30 or bypass the processing region 30. In a specific embodiment, the first external port 42 is the inlet port so that the inlet side of the processing region 30 is closer to the fluid displacement region 50 than the outlet side of the processing region 30.

Figure 9C:
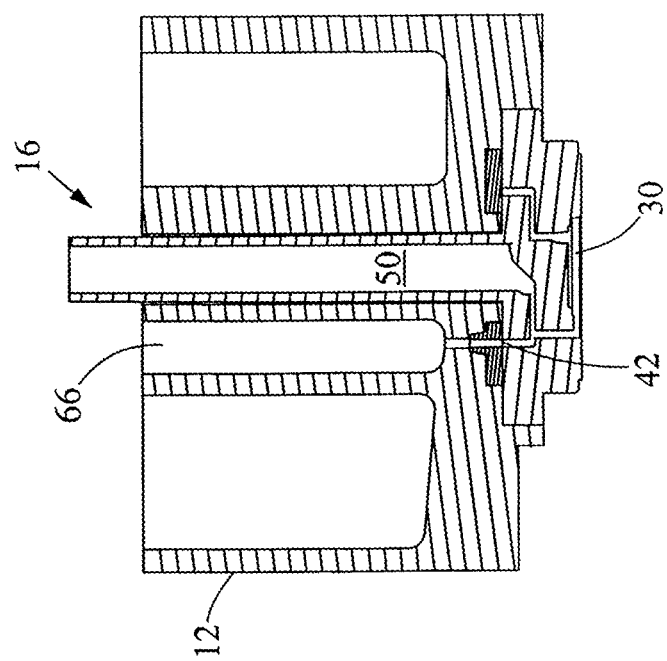
Figure 9C:
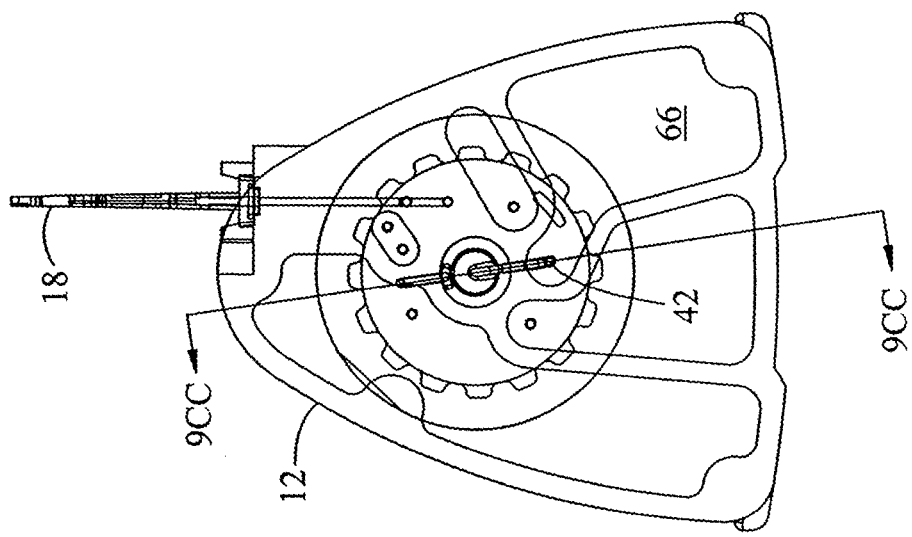

To demonstrate the fluid metering and distribution function of the valve 16, FIGS. 9A-9LL illustrate the operation of the valve 16 for a specific protocol. In FIGS. 9A and 9AA, the first external port 42 is placed in fluidic communication with a sample chamber 60 by rotating the valve 16, and the piston 54 is pulled upward to draw a fluid sample from the sample chamber 60 through the first outer conduit 40 and fluid displacement channel 48 to the fluid displacement region 50, bypassing the processing region 30. For simplicity, the piston 54 is not shown in FIGS. 9A-9LL. The valve 16 is then rotated to place the second external port 46 in fluidic communication with a waste chamber 64 as shown in FIGS. 9B and 9BB. The piston 54 is pushed downward to drive the fluid sample through the fluid processing region 30 to the waste chamber 64. In a specific embodiment, the fluid processing region 30 includes a filter or a filter stack 27 for capturing sample components (e.g., cells, spores, microorganisms, viruses, proteins, or the like) from the fluid sample as it passes therethrough. An example of a filter stack is described in commonly assigned, copending U.S. patent application Ser. No. 09/584,327, entitled "Apparatus and Method for Cell Disruption," filed May 30, 2000, which is incorporated herein by reference in its entirety. In alternative embodiments, other active members may be provided in the processing region 30. These first two steps of capturing sample components may be repeated as desired.

Figure 9D:
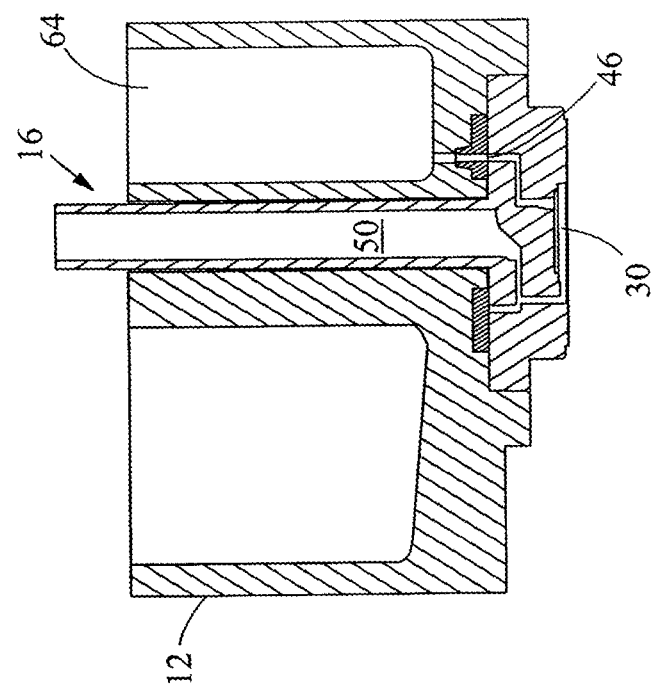
Figure 9D:
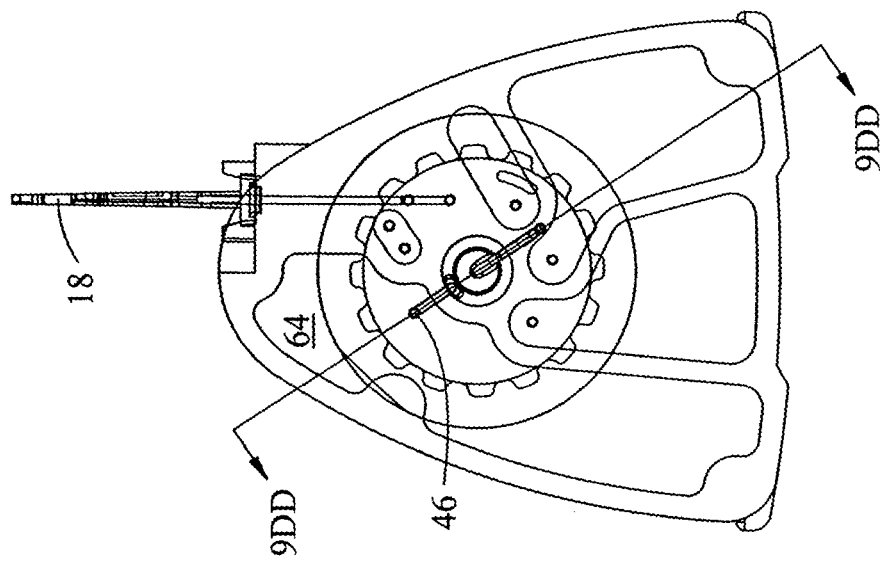

In FIGS. 9C and 9CC, the valve 16 is rotated to place the first external port 42 in fluidic communication with a wash chamber 66, and the piston 54 is pulled upward to draw a wash fluid from the wash chamber 66 into the fluid displacement region 50, bypassing the processing region 30. The valve 16 is then rotated to place the second external port 46 in fluidic communication with the waste chamber 64 as shown in FIGS. 9D and 9DD. The piston 54 is pushed downward to drive the wash fluid through the fluid processing region 30 to the waste chamber 64. The above washing steps may be repeated as desired. The intermediate washing is used to remove unwanted residue within the valve 16.

Figure 9E:
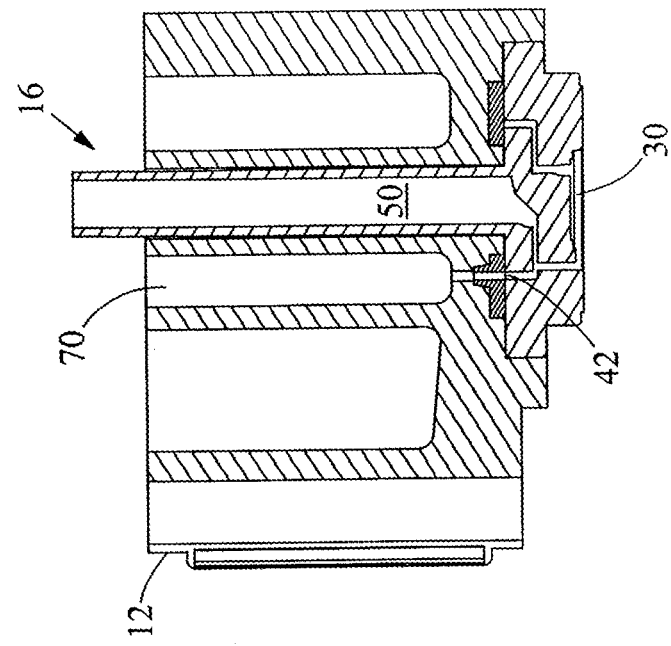
Figure 9E:
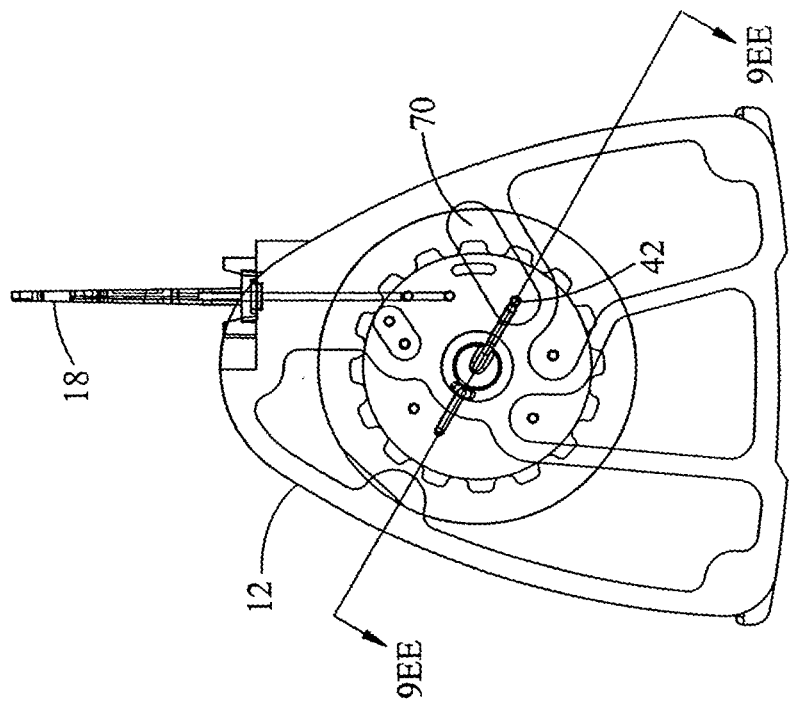
Figure 9G:
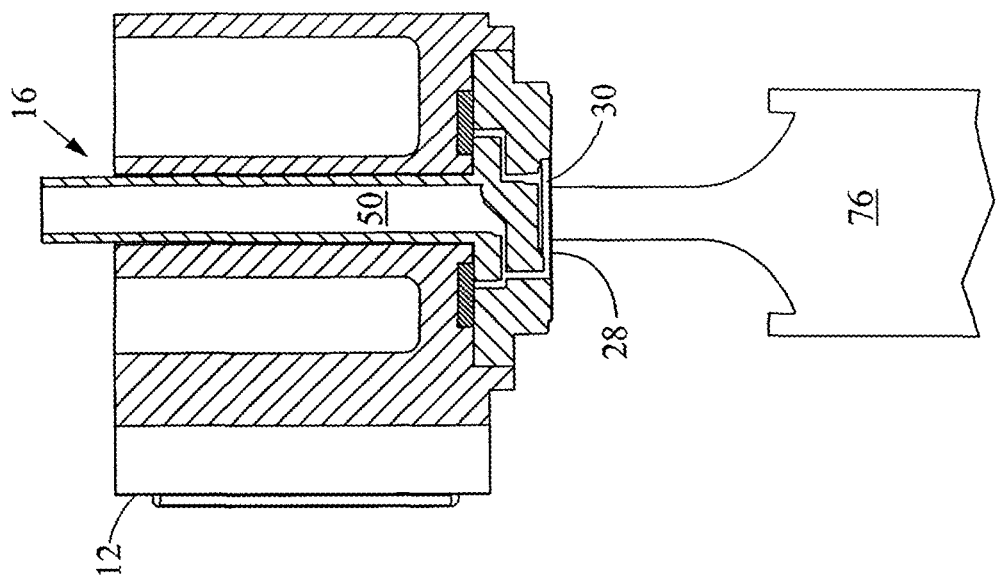
Figure 9G:
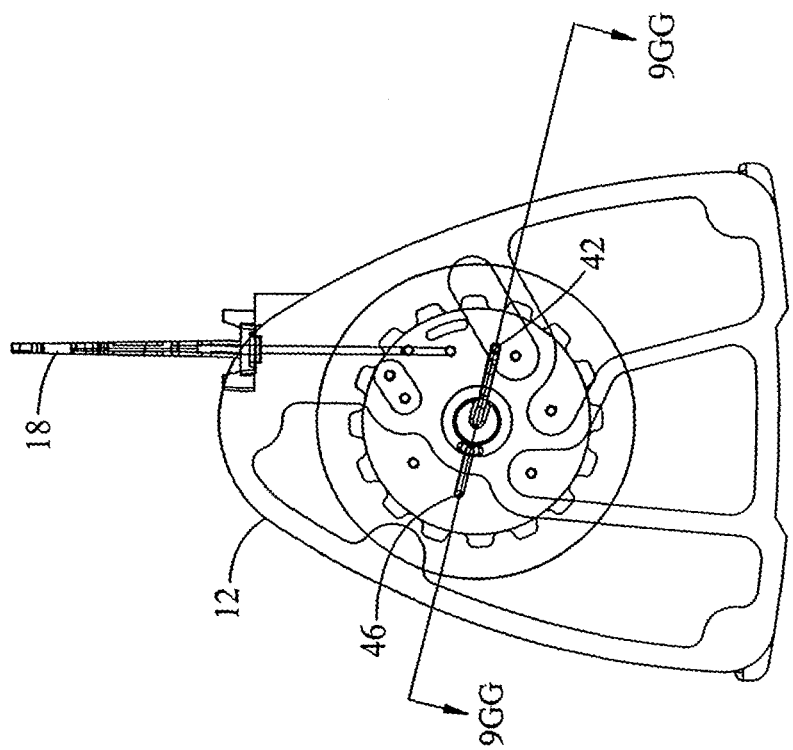

In FIGS. 9E and 9EE, the valve 16 is rotated to place the first external port 42 in fluidic communication with a lysis chamber 70, and the piston 54 is pulled upward to draw a lysing fluid (e.g., a lysing reagent or buffer) from the lysis chamber 70 into the fluid displacement region 50, bypassing the processing region 30. The valve 16 is then rotated to place the second external port 46 in fluidic communication with the waste chamber 64 as shown in FIGS. 9F and 9FF. The piston 54 is pushed downward to drive the lysing fluid through the fluid processing region 30 to the waste chamber 64. In FIGS. 9G, and 9GG, the valve 16 is rotated to close the external ports 42, 46. The piston 54 is pushed downward to pressurize the remaining lysing fluid and the sample components captured in the fluid processing region 30. Additional energy may be applied to the mixture in the processing region 30. For instance, a sonic member 76 such as an ultrasonic horn may be placed in contact with the outer cover 28 to transmit sonic energy into the processing region 30 to facilitate lysing of the sample components. In one embodiment, the outer cover 28 is made of a flexible film which is stretched under pressure to contact the sonic member 76 during lysing to allow transmission of the sonic energy into the processing region 30.

The cover 28 in one embodiment is a flexible film of polymeric material such as polypropylene, polyethylene, polyester, or other polymers. The film may either be layered, e.g., laminates, or the films may be homogeneous. Layered films are preferred because they generally have better strength and structural integrity than homogeneous films. In particular, layered polypropylene films are presently preferred because polypropylene is not inhibitory to polymerase chain reaction (PCR). Alternatively, the cover 28 may comprise other materials such as a rigid piece of plastic. In one preferred embodiment, the cover 28 is an interface wall which is dome-shaped or includes stiffening ribs as shown, for example, in PCT Publication WO 00/73413 entitled "Apparatus and Method for Cell Disruption," or commonly assigned, copending U.S. patent application Ser. No. 09/972, 221, entitled "Apparatus and Method for Rapid Disruption of Cells or Viruses," filed Oct. 4, 2001, the entire disclosures of which are incorporated herein by reference.

In general, the energy transmitting member that is operatively coupled to the processing region 30 for transmitting energy thereto may be an ultrasonic, piezoelectric, magnetostrictive, or electrostatic transducer. The energy transmitting member may also be an electromagnetic device having a wound coil, such as a voice coil motor or a solenoid device. It is presently preferred that the energy transmitting member be a sonic member, such as an ultrasonic horn. Suitable horns are commercially available from Sonics & Materials, Inc. having an office at 53 Church Hill, Newton, Conn. 06470-1614, U.S.A. Alternatively, the sonic member may comprise a piezoelectric disk or any other type of ultrasonic transducer that may be coupled to the cover 28. In alternative embodiments, the energy transmitting member may be a thermal element (e.g., a heater) for transmitting thermal energy to the processing region 30 or an electrical element for transmitting electrical energy to the processing region 30. In addition, multiple energy transmitting members may be employed simultaneously, e.g., simultaneously heating and sonicating the processing region to effect lysis of cells, spores, viruses, or microorganisms trapped in the processing region.

Figure 9H:
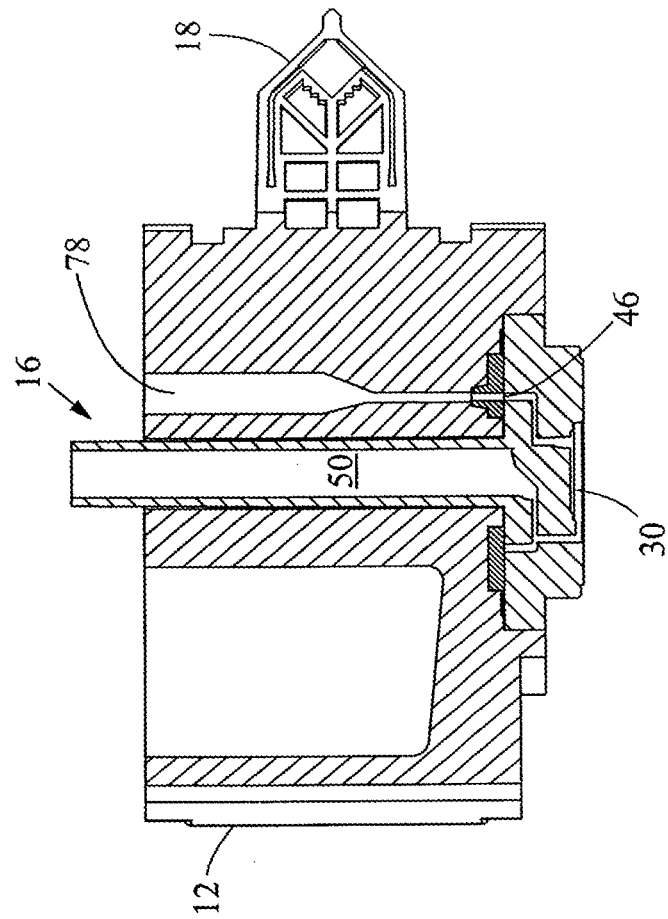
Figure 9H:
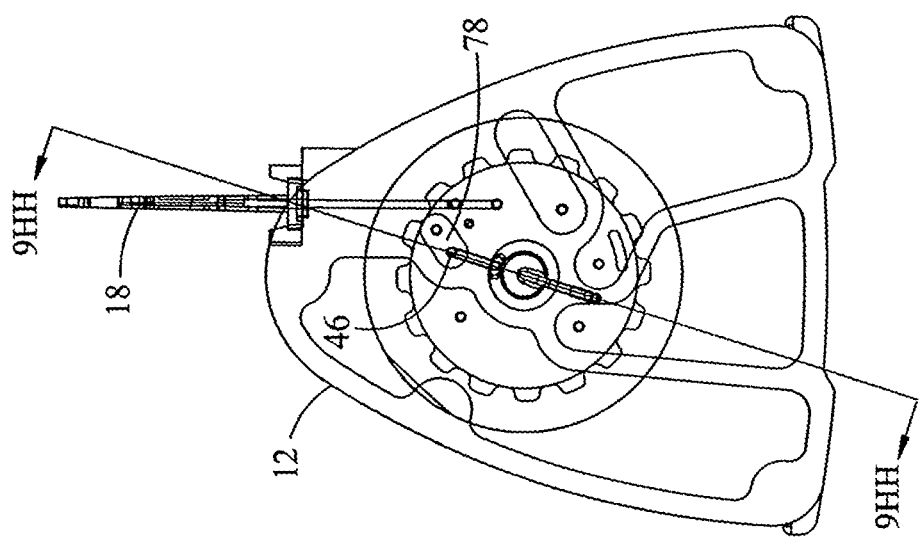
Figure 9J:
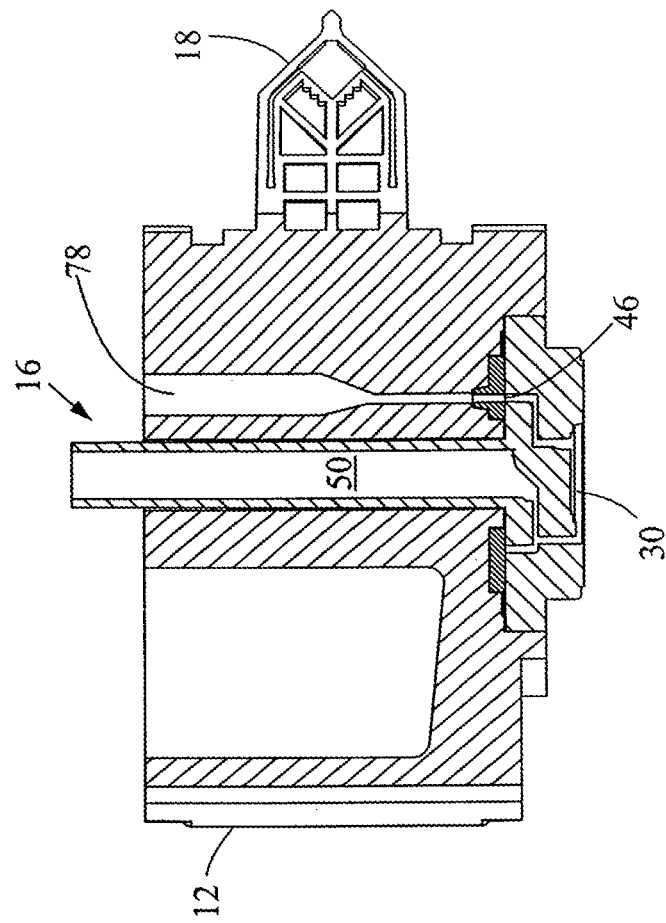
Figure 9J:
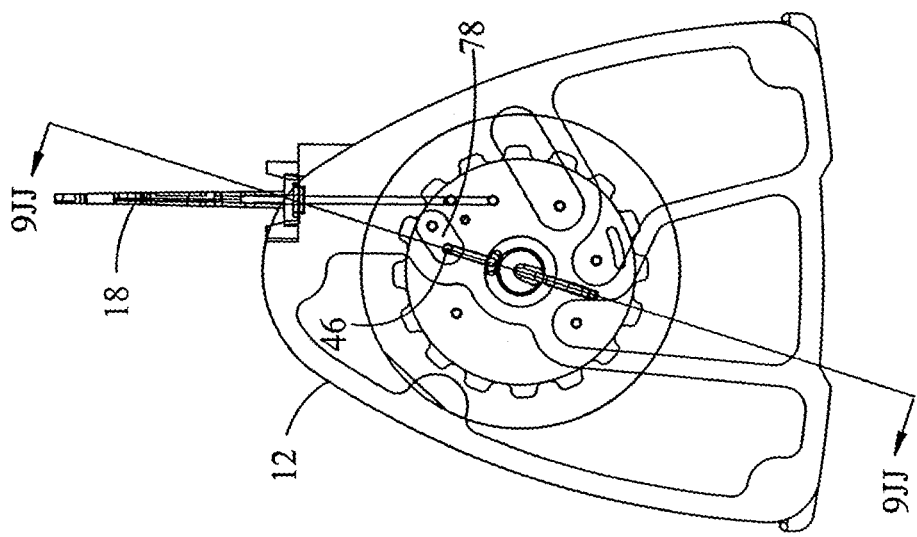

In FIGS. 9H and 9HH, the valve 16 is rotated to place the second external port 46 in fluidic communication with a mastermix or reagent chamber 78, and the piston 54 is pushed downward to elute the mixture from the processing region 30 to the reagent chamber 78. The reagent chamber 78 typically contains reagents (e.g., nucleic acid amplification reagents and probes) to be mixed with the sample. Any excess mixture is dispensed into the waste chamber 64 via the second external port 46 after rotating the valve 16 to place the port 46 in fluidic communication with the waste chamber 64, as shown in FIGS. 9I and 9II. The mixture is then mixed in the reagent chamber 78 by toggling. This is carried out by placing the fluid displacement region 50 in fluidic communication with the reagent chamber 78 as shown in FIGS. 9J and 9JJ, and moving the piston 54 up and down. Toggling of the mixture through the filter in the processing region 30, for instance, allows larger particles trapped in the filter to temporarily move out of the way to permit smaller particles to pass through. The reagent chamber 78 may contain dried or lyophilized reagents that are reconstituted when mixed with fluid.

In FIGS. 9K, 9KK, and 9K'K', the valve 16 is rotated to place the first external port 42 in fluidic communication with a first branch 84 coupled to the reaction vessel 18, while the second branch 86 which is coupled to the reaction vessel 18 is placed in fluidic communication with the crossover groove 56. The first branch 84 and second branch 86 are disposed at different radii from the axis 52 of the valve 16, with the first branch 84 having a common radius with the first external port 42 and the second branch 86 having a common radius with the crossover groove 56. The crossover groove 56 is also in fluidic communication with the reagent chamber 78 (FIG. 9K), and serves to bridge the gap between the reagent chamber 78 and the second branch 86 to provide crossover flow therebetween. The external ports are disposed within a range of external port radii from the axis and the crossover groove is disposed within a range of crossover groove radii from the axis, where the range of external port radii and the range of crossover groove radii are non-overlapping. Placing the crossover groove 56 at a different radius from the radius of the external ports 42, 46 is advantageous because it avoids cross-contamination of the crossover groove 56 by contaminants that may be present in the area near the surfaces between the valve 16 and the housing 12 at the radius of the external ports 42, 46 as a result of rotational movement of the valve 16. Thus, while other configurations of the crossover groove may be used including those that overlap with the radius of the external ports 42, 46, the embodiment as shown is a preferred arrangement that isolates the crossover groove 56 from contamination from the area near the surfaces between the valve 16 and the housing 12 at the radius of the external ports 42, 46.

To fill the reaction vessel 18, the piston 54 is pulled upward to draw the mixture in the reagent chamber 78 through the crossover groove 56 and the second branch 86 into the reaction vessel 18. In such an arrangement, the reaction vessel 18 is the aspiration chamber or referred to as the first chamber, and the reagent chamber 78 is the source chamber or referred to as the second chamber. The valve 16 is then rotated to place the second external port 46 in fluidic communication with the first branch 84 and to close the first external port 42, as shown in FIGS. 9L and 9LL. The piston 54 is pushed downward to pressurize the mixture inside the reaction vessel 18. The reaction vessel 18 may be inserted into a thermal reaction chamber for performing nucleic acid amplification and/or detection. The two branches 84, 86 allow filling and evacuation of the reaction chamber of the reaction vessel 18. The vessel maybe connected to the housing 12 by ultrasonic welding, mechanical coupling, or the like, or be integrally formed with the housing 12 such as by molding. The use of a reaction vessel for analyzing a fluid sample is described in commonly assigned, copending U.S. patent application Ser. No. 09/584,328, entitled "Cartridge for Conducting a Chemical Reaction," filed May 30, 2000.

To operate the valve 16 of FIGS. 3-8, a motor such as a stepper motor is typically coupled to the toothed periphery 29 of the disk portion 22 to rotate the valve 16 relative to the housing 12 for distributing fluid with high precision. The motor can be computer-controlled according to the desired protocol. A linear motor or the like is typically used to drive the piston 54 up and down with precision to provide accurate metering, and may also be computer-controlled according to the desired protocol.

Figure 10:
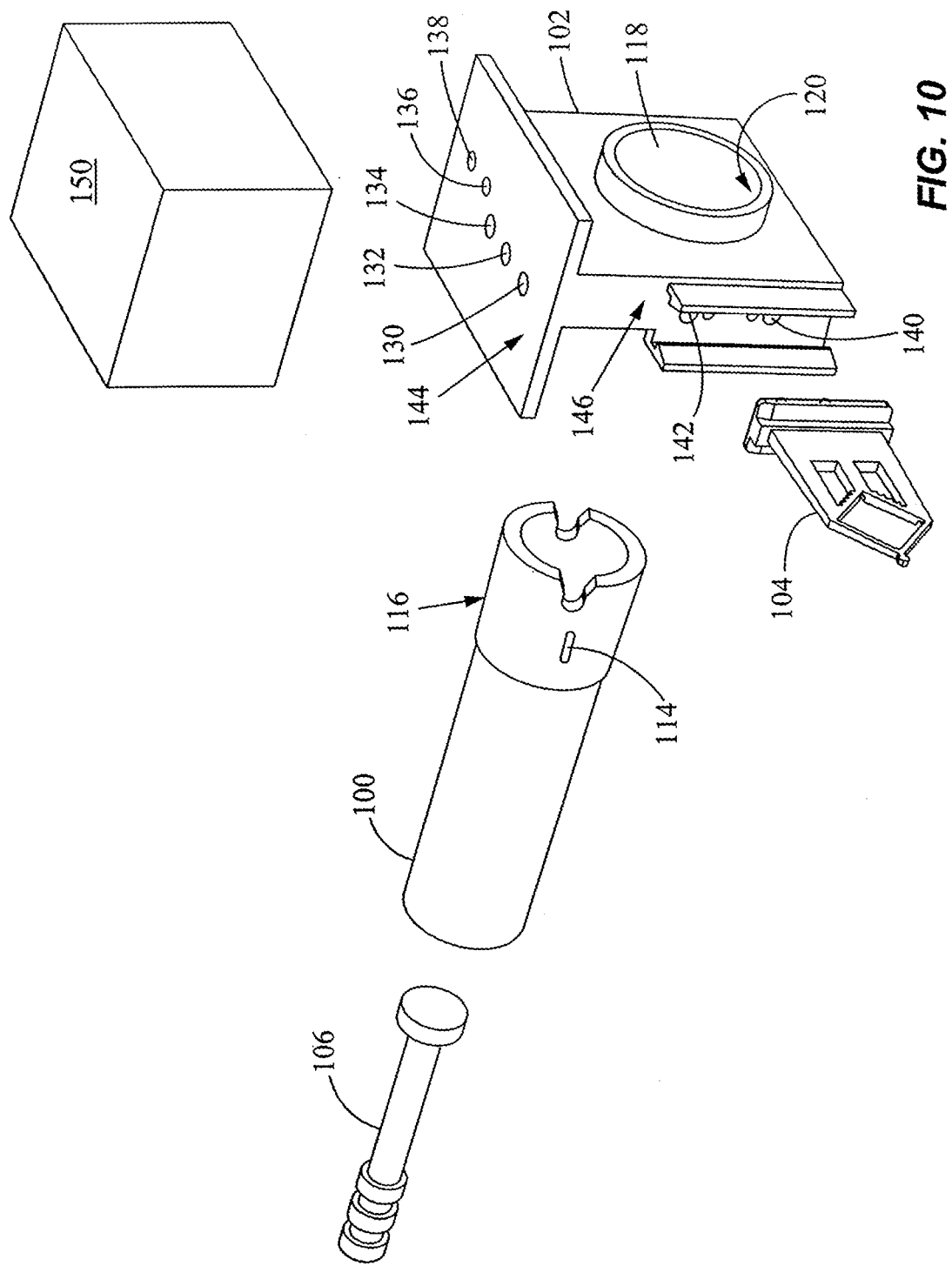
FIG. 10 is an exploded perspective view of the fluid control and processing system according to another embodiment of the present invention.
Figure 11:
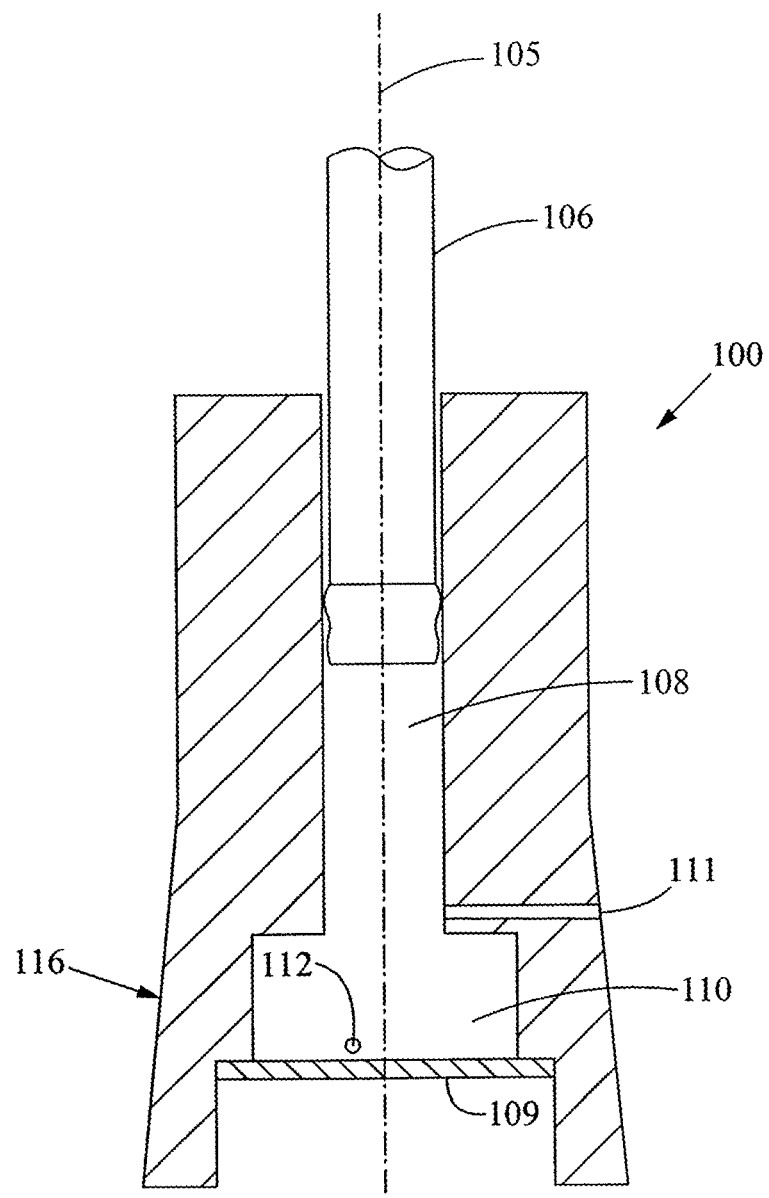
FIG. 11 is a cross-sectional view of a fluid control apparatus in the system of FIG. 10.

FIG. 10 shows another valve 100 which is rotatably coupled to a fluid control channel housing or block 102. A reaction vessel 104 is detachably coupled to the housing 102. The valve 100 is a generally tubular member with a longitudinal axis 105 as shown in FIG. 11. A piston 106 is movably connected to the valve 100 to change the volume of the fluid displacement region 108 as the piston 106 is moved up and down. A cover 109 is placed near the bottom of the valve 100. A fluid processing region 110 is disposed in the valve 100 and is in continuous fluidic communication with the fluid displacement region 108. The valve 100 includes a pair of apertures serving as a first port 111 and a second port 112, as best seen in FIG. 11. In the embodiment shown, the ports 111, 112 are angularly spaced by about 120°, but the spacing may be different in alternate embodiments. A crossover channel or groove 114 is formed on the external surface 116 of the valve 100 and extends generally in the longitudinal direction, as seen in FIG. 10. The two ports 111, 112 are disposed at different levels longitudinally offset from one another along the longitudinal axis 105, and the crossover groove 114 extends in the longitudinal direction of the axis 105 bridging the two levels of the ports 111, 112.

The housing 102 has an opening 118 for receiving the portion of the valve 100 having the ports 111, 112 and groove 114. The internal surface 120 around the opening 118 is shaped to cooperate with the external surface 116 of the valve 100. Although a gasket may be placed between the internal surface 120 and the external surface 116, a preferred embodiment employs tapered or conical surfaces 120, 116 that produce a sealing effect without the use of an additional gasket. The housing 102 includes a plurality of channels and ports and the valve 100 is rotatable around its axis 105 to allow the ports 111, 112 to be placed selectively in fluidic communication with the plurality of channels in the housing 102. Depending on which port is opened or closed and whether the piston 106 is moved upward or downward, the fluid flow in the valve 100 can change directions, and the ports 111, 112 can each switch from being an inlet port to an outlet port.

Figure 12A:
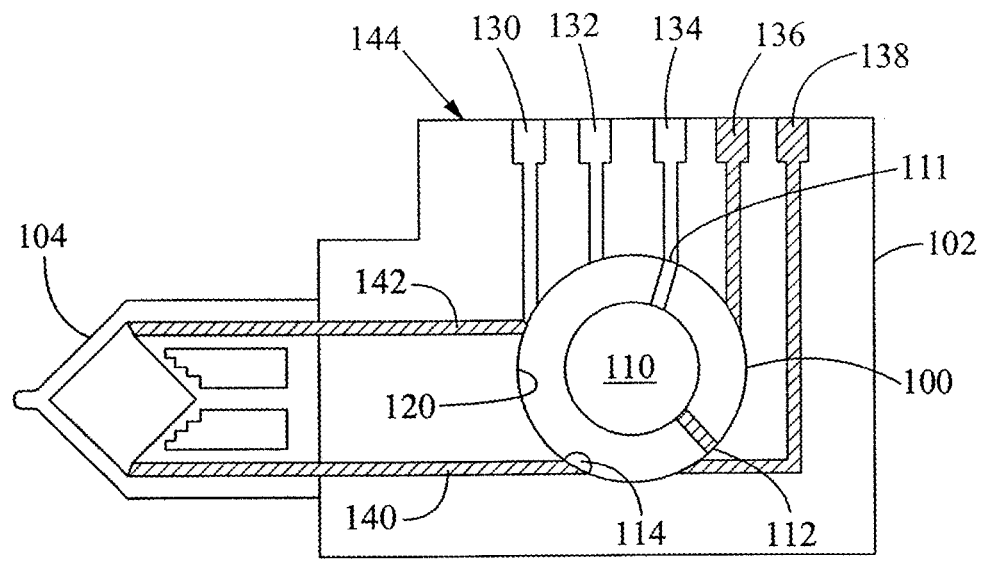
FIGS. 12A-12N are plan views illustrating a specific protocol for controlling and processing fluid using the fluid control and processing system of FIG. 10.
Figure 12B:
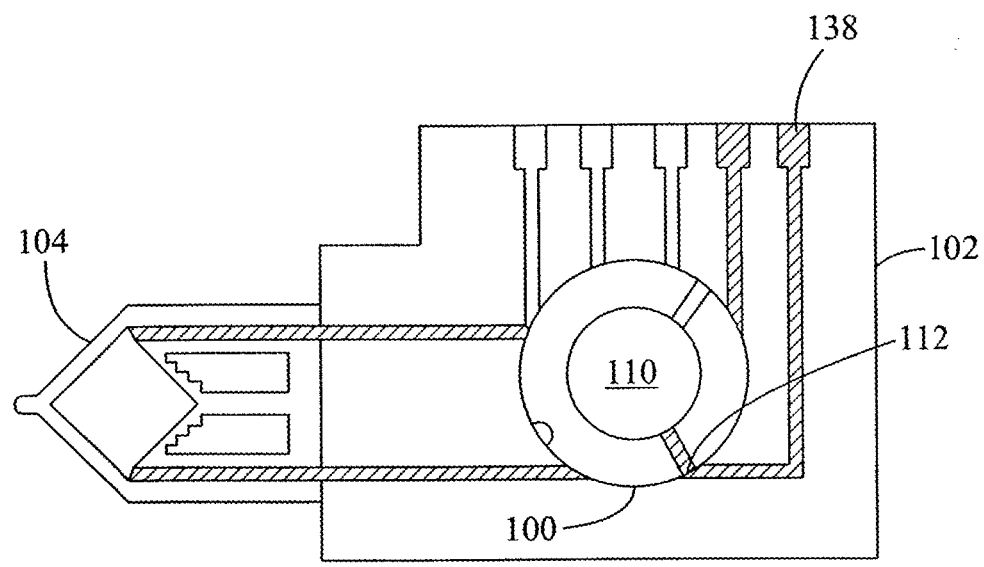
Figure 12C:
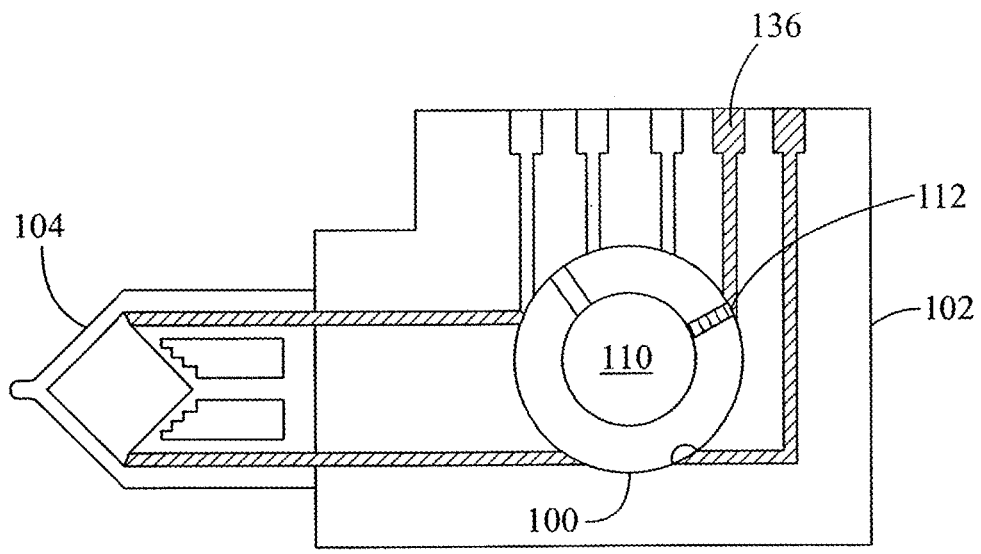
Figure 12D:
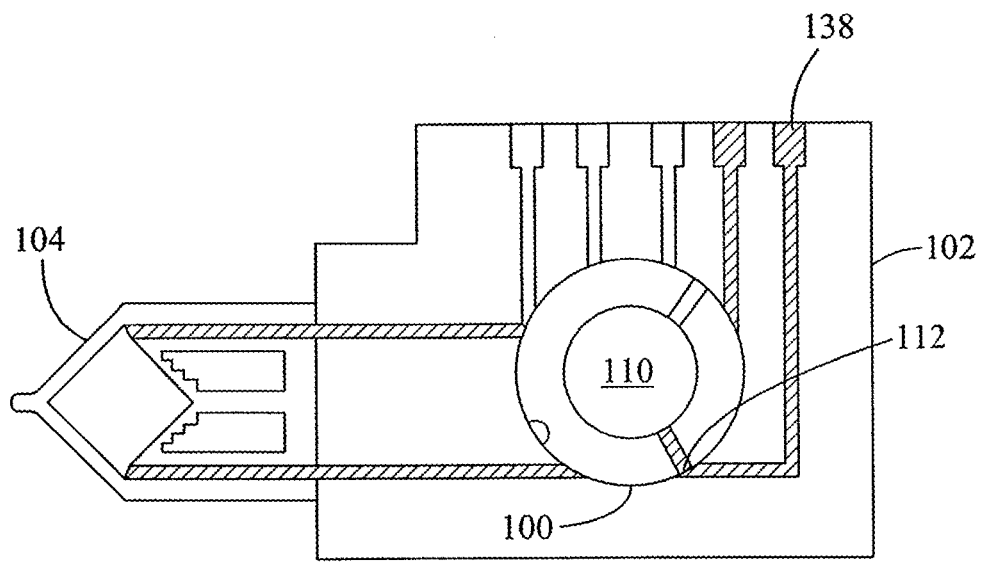
Figure 12E:
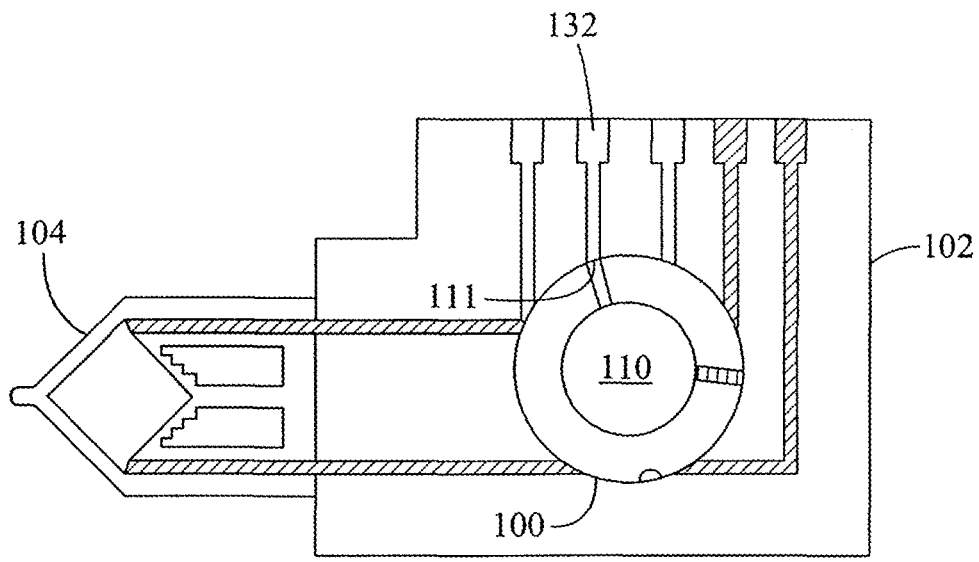
Figure 12F:
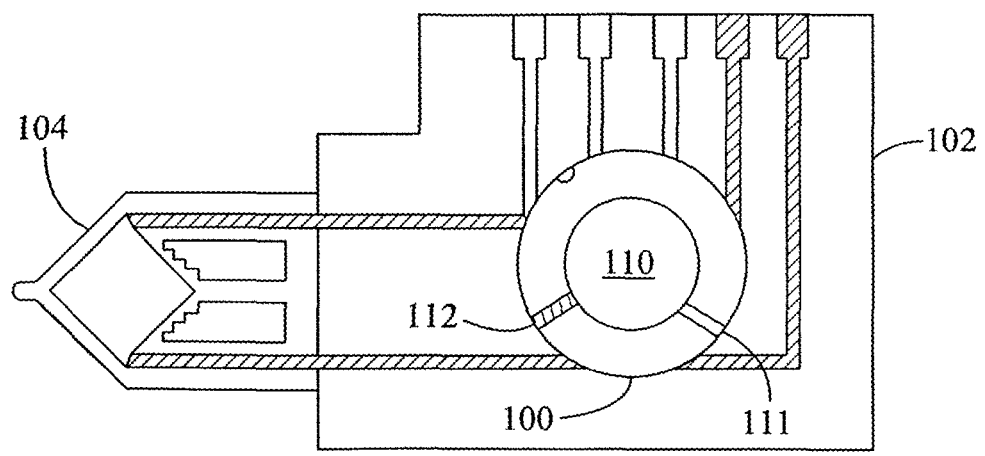
Figure 12G:
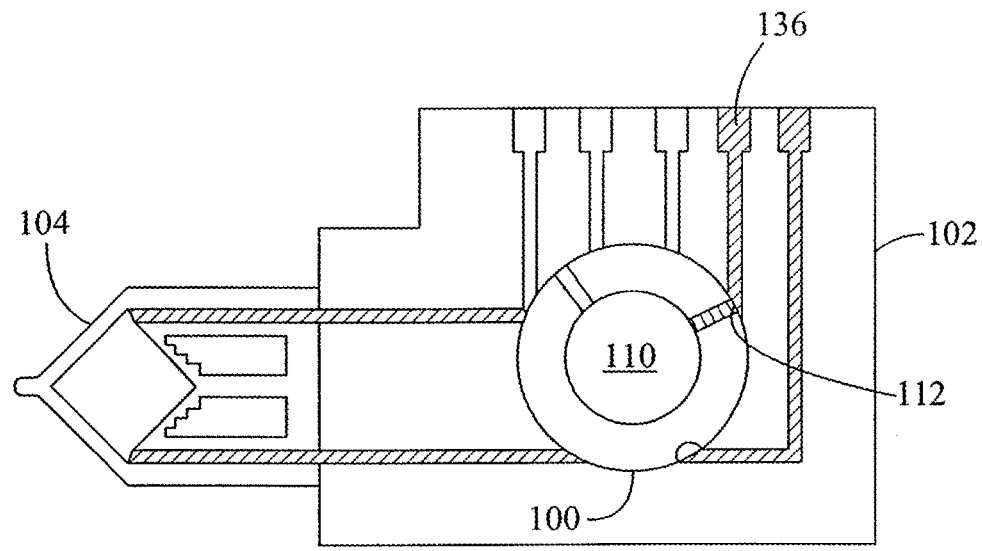
Figure 12H:
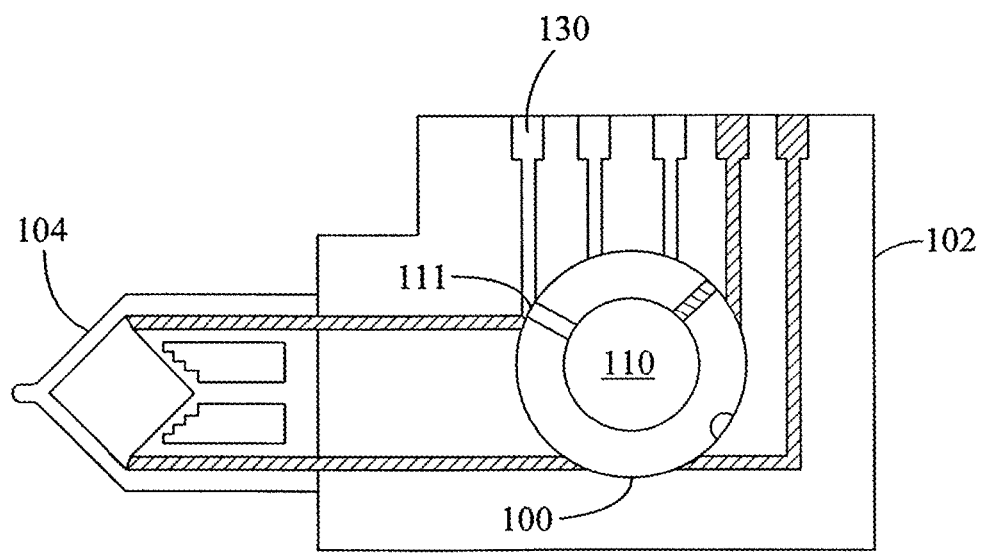
Figure 12I:
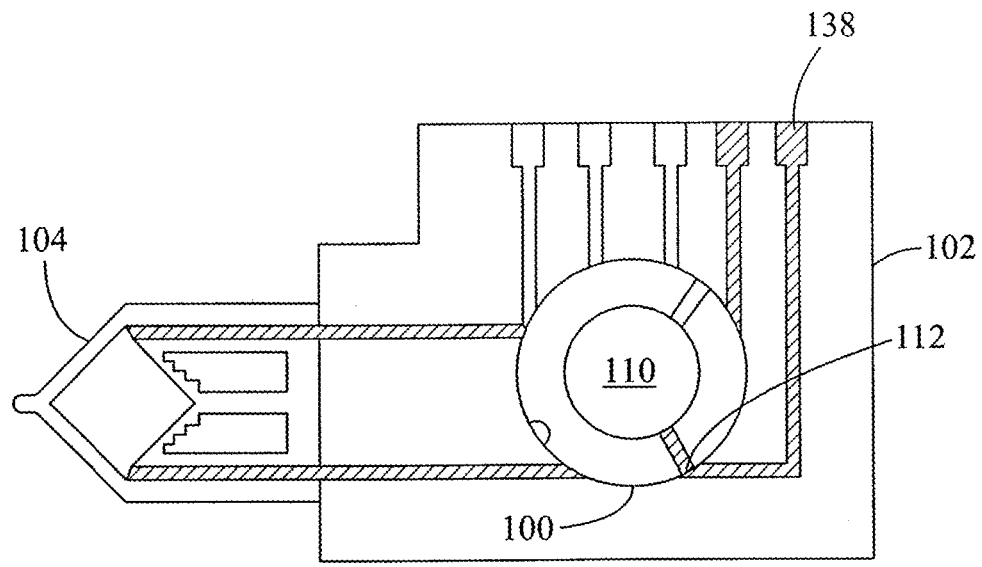
Figure 12J:
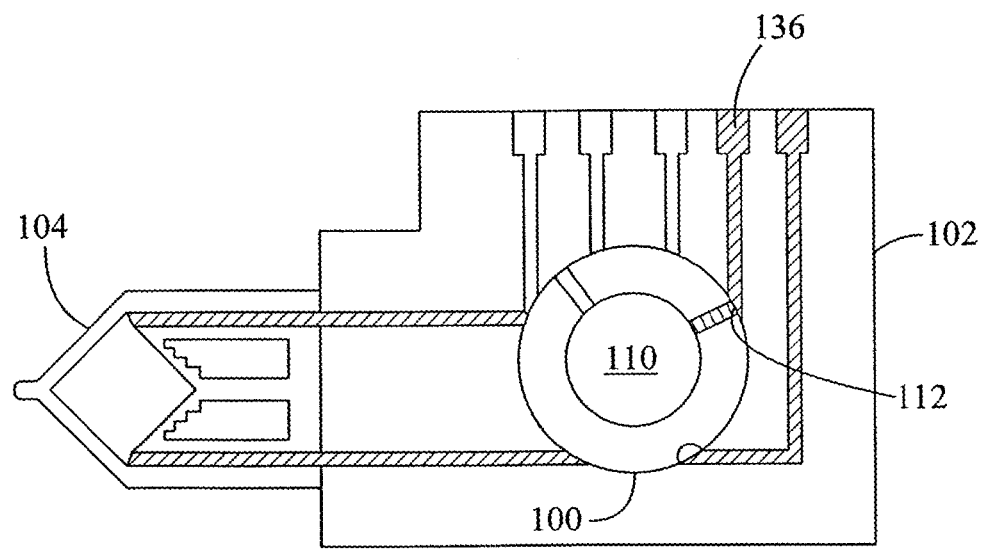
Figure 12K:
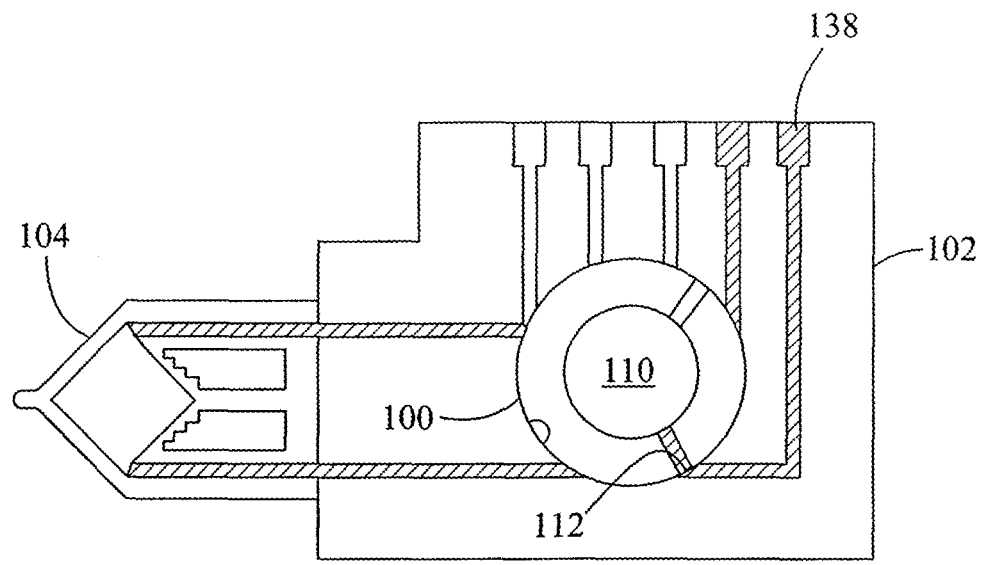
Figure 12L:
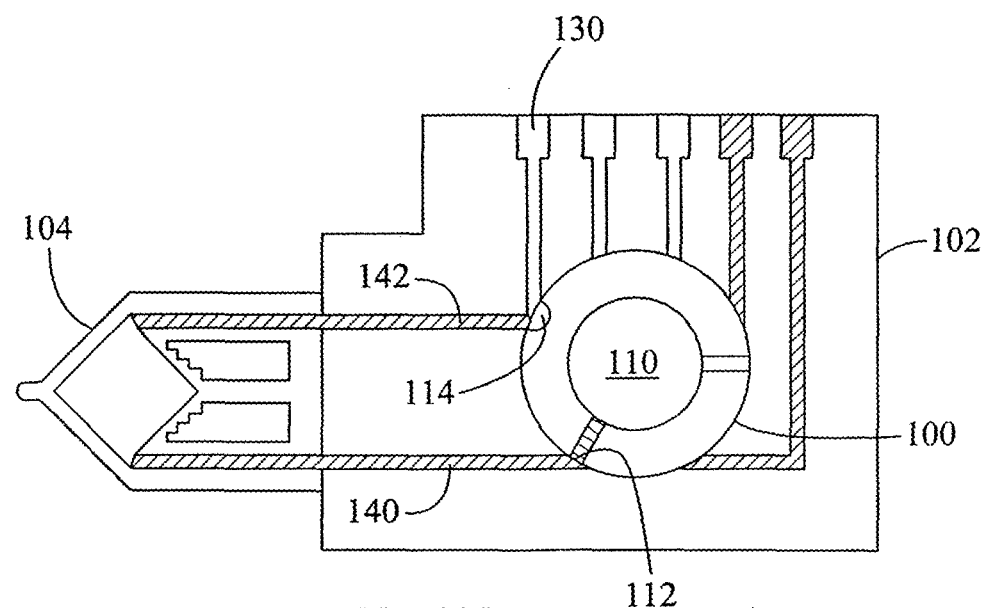
Figure 12M:
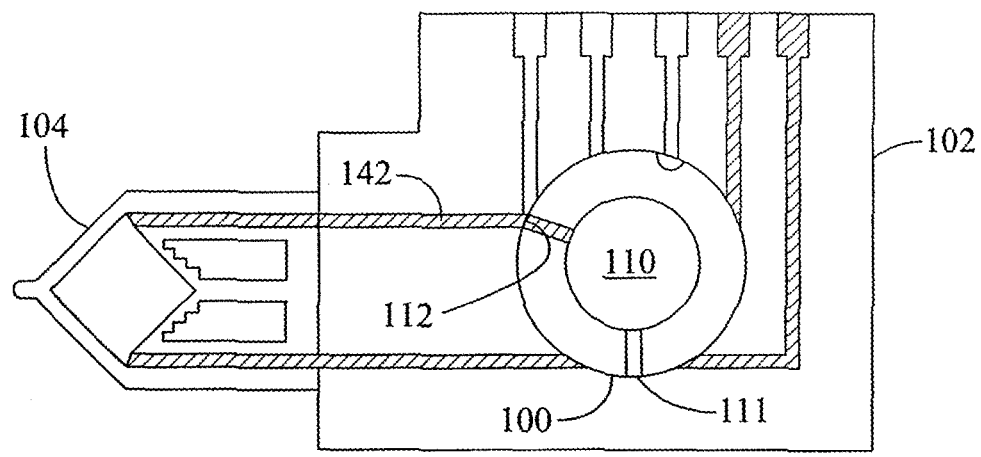
Figure 12N:
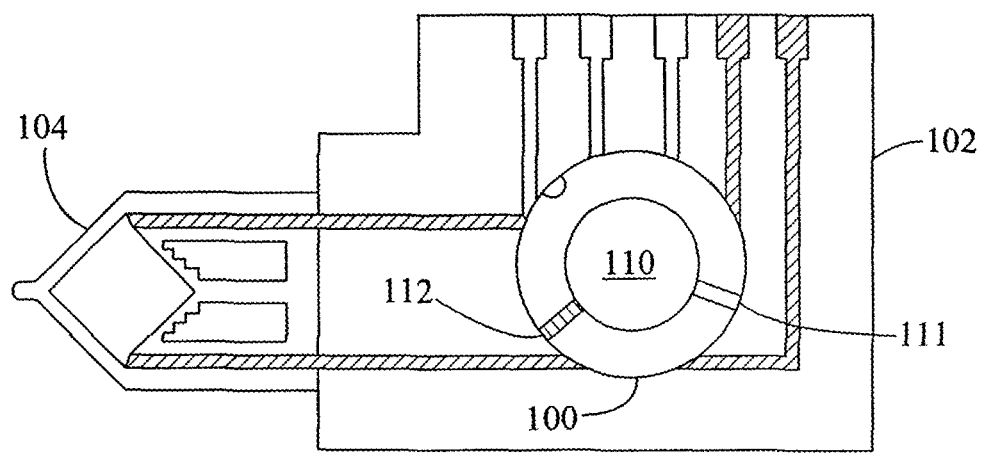

To demonstrate the fluid metering and distribution function of the valve 100, FIGS. 12A-12N illustrate the operation of the valve 100 for a specific protocol. As shown in FIG. 12A, the housing 102 includes a plurality of fluid channels. For convenience, the channels are labeled as follows: reagent channel 130, lysing channel 132, sample channel 134, wash channel 136, waste channel 138, first branch 140, and second branch 142. The channels 130-138 extend from the internal surface 120 to one external surface 144 which is generally planar, and the branches 140, 142 extend from the internal surface 120 to another external surface 146 which is also generally planar (FIG. 10). When assembled, the first port 111 and the channels 130-134 lie on a first transverse plane that is perpendicular to the longitudinal axis 105, while the second port 112, the channels 136, 138, and the two branches 140, 142 lie on a second transverse plane that is perpendicular to the longitudinal axis 105. The second transverse plane is longitudinally offset from the first transverse plane. For convenience, the second port 112, the channels 136, 138, and the branches 140, 142 are shaded to indicate that they are longitudinally offset from the first port 111 and the channels 130-134. The crossover groove 114 extends longitudinally to bridge the offset between the first and second transverse planes. A chamber body 150 is connected to the housing 102 (FIG. 10), and includes the reagent chamber, lysis chamber, sample chamber, wash chamber, and waste chamber that are respectively coupled fluidicly with the channels 130-138. The first and second branches 140, 142 are fluidically coupled with the reaction vessel 104.

In FIG. 12A, the first port 111 is placed in fluidic communication with the sample channel 134 and the piston 106 is pulled upward to draw a fluid sample into the fluid displacement region 108 (FIG. 11). The valve 100 is then rotated to place the second port 112 in fluidic communication with the waste channel 138 and the piston 106 is pushed downward to drive the fluid sample from the displacement region 108 through the processing region 110, and out through the waste channel 138, as shown in FIG. 12B. These steps are typically repeated until an entire sample is processed through the processing region 110, for instance, to capture sample components on a trapping member such as a filter.

In FIG. 12C, the valve 100 is rotated to place the second port 112 in fluidic communication with the wash channel 136 to aspirate a wash fluid into the processing region 110 by pulling the piston 106 upward. The valve 100 is then rotated to place the second port 112 in fluidic communication with the waste channel 138 and the piston 106 is pushed downward to drive the wash fluid from the processing region 110 out through the waste channel 138. The above washing steps can be repeated as desired to remove unwanted residue inside the valve 100.

For lysing, the valve 100 is rotated to place the first port 111 in fluidic communication with the lysing channel 132 and the piston 106 is pulled upward to draw a lysing fluid into the fluid displacement region 108, as shown in FIG. 12E. In FIG. 12F, the valve 110 is rotated to close both ports 111, 112. The piston 106 is pushed downward to push the lysing fluid into the processing region 110 and to pressurize the lysing fluid and the sample components captured in the fluid processing region 110. Additional energy may be applied to the mixture in the processing region 110 including, for instance, sonic energy transmitted into the processing region 110 by operatively coupling a sonic member with the cover 109 (FIG. 11).

In FIG. 12G, a desired preset amount of wash fluid is aspirated into the processing region 110 from the wash channel 136 through the second port 112 to dilute the mixture. The valve 100 is then rotated to place the first port 111 in fluidic communication with the reagent channel 130 to discharge a preset amount of the mixture from the processing region 110 to the reagent chamber, as shown in FIG. 12H. The piston 106 is moved up and down to agitate and mix the mixture by toggling. The balance of the mixture is discharged through the second port 112 to the waste channel 138, as shown in FIG. 12I. Another wash is performed by drawing a wash fluid from the wash channel 136 through the second port 112 into the processing region 110 (FIG. 12J), and discharging the wash fluid from the processing region 110 through the second port 112 to the waste channel 138 (FIG. 12K).

In FIG. 12L, the valve 100 is rotated to place the second port 112 in fluidic communication with the first branch 140 coupled to the reaction vessel 104, while the second branch 142 which is coupled to the reaction vessel 104 is placed in fluidic communication with the crossover groove 114. The second branch 142 is longitudinal offset from the reagent channel 130. In the position as shown in FIG. 12L, the crossover groove 114 extends longitudinally to bridge the offset between the second branch 142 and the reagent channel 130 to place them in fluidic communication with one another. As a result, the fluid processing region 110 is in fluidic communication, through the first branch 140, the reaction vessel 104, the second branch 142, and the crossover groove 114, with the reagent channel 130.

By pulling the piston 106 upward, the mixture in the reagent chamber is drawn from the reagent channel 130 through the crossover groove 114 and the second branch 142 into the reaction vessel 104. The valve 100 is then rotated to place the second port 112 in fluidic communication with the second branch 142 and to close the first port 111, as shown in FIG. 12M. The piston 106 is pushed downward to pressurize the mixture inside the reaction vessel 104. In FIG. 12N, the valve 100 is rotated to close the ports 111, 112 and isolate the reaction vessel 104. The reaction vessel 104 may be inserted into a thermal reaction chamber for performing nucleic acid amplification and/or detection.

As illustrated in the above embodiments, the fluid control and processing system is advantageously a fully contained system that is versatile and adaptable. The fluid displacement region is the motivating force for moving fluid in the system. By maintaining a continuous fluidic communication between the fluid displacement region and the fluid processing region, the motivating force for moving fluid in the system is fluidicly coupled to the processing region at all times. The fluid displacement region (motivating force) also acts as a temporary storage area for the fluid being driven through the system. While the embodiments shown employ a moving piston in the fluid displacement region as the motivating force, other mechanisms may be used including, e.g., pneumatic pump mechanisms or the like which use pressure as the motivating force without a change in volume of the fluid displacement region. The inlet or outlet side of the fluid processing region can address any of the chambers to permit random access to reagents and other fluids. Complex protocols can be programmed relatively easily into a computer controller and then executed using the versatile fluid control and processing system. A myriad of different protocols can be performed using a single platform.

In the embodiments shown, the fluid control occurs by addressing a pair of ports in the valve to place only one port at a time selectively in fluidic communication with the chambers. This is accomplished by keeping the pair of ports out of phase relative to the chambers. A crossover or bypass channel provides additional fluid control capability (e.g., allowing convenient filling and emptying of the reaction vessel within the closed system). Of course, different porting schemes may be used to achieve the desired fluid control in other embodiments. Moreover, while the embodiments shown each include a single fluid processing region in the valve body, additional processing regions can be located in the valve body if desired. Generally, the valve body needs (n+1) ports per n processing regions.

The use of a single valve produces high manufacturing yields due to the presence of only one failure element. The concentration of the fluid control and processing components results in a compact apparatus (e.g., in the form of a small cartridge) and facilitates automated molding and assembly. As discussed above, the system advantageously includes dilution and mixing capability, intermediate wash capability, and positive pressurization capability. The fluid paths inside the system are normally closed to minimize contamination and facilitate containment and control of fluids within the system. The reaction vessel is conveniently detachable and replaceable, and may be disposable in some embodiments.

The components of the fluid control and processing system may be made of a variety of materials that are compatible with the fluids being used. Examples of suitable materials include polymeric materials such as polypropylene, polyethylene, polycarbonate, acrylic, or nylon. The various chambers, channels, ports, and the like in the system may have various shapes and sizes.

The above-described arrangements of apparatus and methods are merely illustrative of applications of the principles of this invention and many other embodiments and modifications may be made without departing from the spirit and scope of the invention as defined in the claims.

Figure 13:
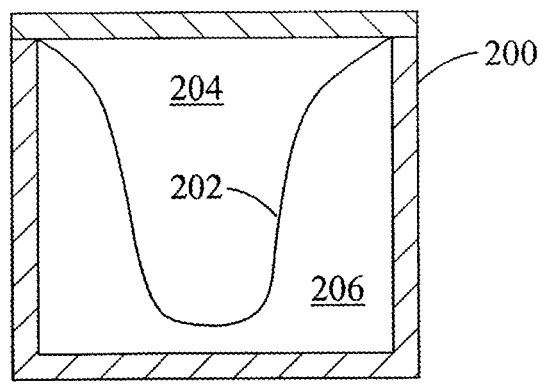
FIG. 13 is a cross-sectional view of a soft-walled chamber.

For instance, FIG. 13 shows a soft-walled chamber 200 that may be incorporated into the fluid control and processing system. Typically, an on-board reagent style cartridge requires a total fluid volume of at least twice the total volume of reagents and sample combined in rigid systems. The use of soft-walled chambers can reduce the required volume. These chambers have flexible walls, and can typically be formed using films and thermoforming. An added advantage of soft walls is that venting need not be provided if the walls are sufficiently flexible to allow them to collapse when the chamber is emptied. In FIG. 13, a flexible sidewall 202 separates a reagent chamber 204 and a waste chamber 206. Because the waste is composed of the sample and reagents, the volume required for waste is no more than the sum of the sample and reagents. The reagent chamber 204 contracts while the waste chamber 206 expands, and vice versa. This can be a closed system with no connection to the exterior. The configuration can reduce the overall size of the cartridge, and can allow fast change-overs of chamber volumes. It can also eliminate venting, and can cut costs by reducing the number of platforms that would otherwise need to be built with hard tooling. In one embodiment, at least two of the plurality of chambers in the system are separated by a flexible wall to permit change-over of chamber volumes between the chambers.

Figure 14:
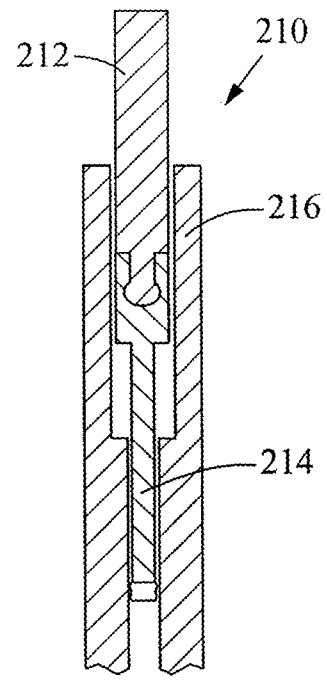
FIG. 14 is a cross-sectional view of a piston assembly.

FIG. 14 shows a piston assembly 210 including a piston rod 212 connected to a piston shaft 214 having a smaller cross-section than the rod 212 for driving small amounts of fluids. The thin piston shaft 214 may bend under an applied force if it is too long. The piston rod 212 moves along the upper portion of the barrel or housing 216, while the piston shaft 214 moves along the lower portion of the barrel 216. The movement of the piston rod 212 guides the movement of the piston shaft 214, and absorbs much of the applied force so that very little bending force is transmitted to the thin piston shaft 214.

Figure 15:
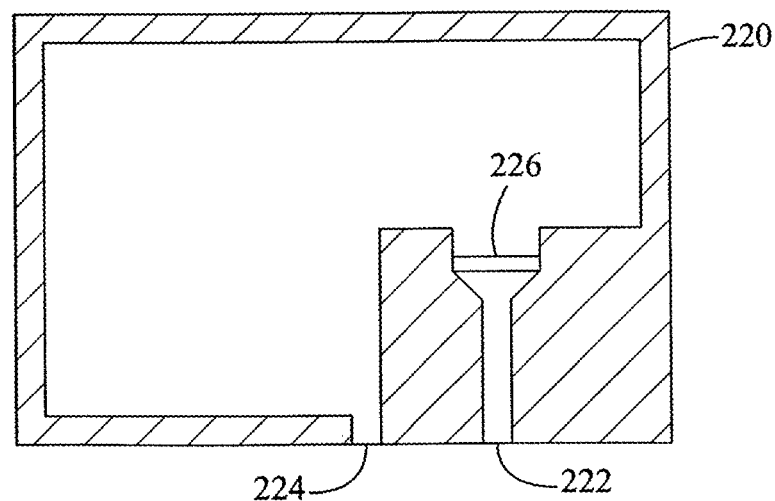
FIG. 15 is a cross-sectional view of a side filtering chamber.

FIG. 15 shows a side chamber 220 that may be incorporated into the system. The side chamber 220 includes an inlet port 222 and an outlet port 224. In this example, the side chamber 220 includes a filter 226 disposed at the inlet port 222. Fluid is directed to flow via the inlet port 222 into the side chamber 220 and out via the outlet port 224 for side filtering. This allows filtering of a fluid sample or the like using the fluid control system of the invention. The fluid may be recirculated to achieve better filtering by the filter 226. This prefiltering is useful to remove particles before introducing the fluid into the main chambers of the system to prevent clogging. The use of a side chamber is advantageous, for instance, to avoid contaminating the valve and the main chambers in the system.

A fluid sample may be introduced into the housing 12 of the fluid control and processing system 10, which may be configured as a cartridge, by a variety of mechanisms, manual or automated. For manual addition, a measured volume of material may be placed into a receiving area of the housing 12 (e.g., one of the plurality of chambers) through an input port and a cap is then placed over the port. Alternatively, the receiving area may be covered by a rubber or similar barrier and the sample is injected into the receiving area by puncturing the barrier with a needle and injecting the sample through the needle. Alternatively, a greater amount of sample material than required for the analysis can be added to the housing 12 and mechanisms within the housing 12 can effect the precise measuring and aliquoting of the sample needed for the specified protocol.

It may be desirable to place certain samples, such as tissue biopsy material, soil, feces, exudates, and other complex material into another device or accessory and then place the secondary device or accessory into the housing causing a mechanical action which effects a function such as mixing, dividing, or extraction. For example, a piece of tissue may be placed into the lumen of a secondary device that serves as the input port cap. When the cap is pressed into the port, the tissue is forced through a mesh that slices or otherwise divides the tissue.

For automated sample introduction, additional housing or cartridge design features are employed and, in many cases, impart sample collection functionality directly into the housing. With certain samples, such as those presenting a risk of hazard to the operator or the environment, such as human retrovirus pathogens, the transfer of the sample to the housing may pose a risk. Thus, in one embodiment, a syringe or sipper may be integrated into the device to provide a means for moving a sample directly into the housing. Alternatively, the device may include a venous puncture needle and a tube forming an assembly that can be used to acquire a sample. After collection, the tube and needle are removed and discarded, and the housing 12 is then placed in an instrument to effect processing. The advantage of such an approach is that the operator or the environment is not exposed to pathogens.

The input port can be designed with a consideration of appropriate human factors as a function of the nature of the intended specimen. For example, respiratory specimens may be acquired from the lower respiratory tract as expectorants from coughing, or as swab or brush samples from the back of the throat or the nares. In the former case, the input port can be designed to allow the patient to cough directly into the housing 12 or to otherwise facilitate spitting of the expectorated sample into the housing. For brush or swab specimens, the specimen is placed into the input port where features of the port and closure facilitate the breaking off and retaining of the end of the swab or brush in the cartridge receiving area.

In another embodiment, the housing 12 includes one or more input tubes or sippers that may be positioned in a sample pool so that the sample material flows into the housing 12. Alternatively, a hydrophilic wicking material can function to draw a sample into the device. For example, the entire cartridge can be immersed directly into the sample, and a sufficient amount of sample is absorbed into the wicking material and wicks into the housing 12. The housing is then removed, and can be transported to the laboratory or analyzed directly using a portable instrument. In another embodiment, tubing can be utilized so that one end of the tube is in direct communication with the housing to provide a fluidic interface with at least one chamber and the other end is accessible to the external environment to serve as a receiver for sample. The tube can then be placed into a sample and serve as a sipper. Thus, the device may include a variety of features for collecting a sample from various different sources and for moving the sample into the housing 12, thereby reducing handling and inconvenience.

Figure 16:
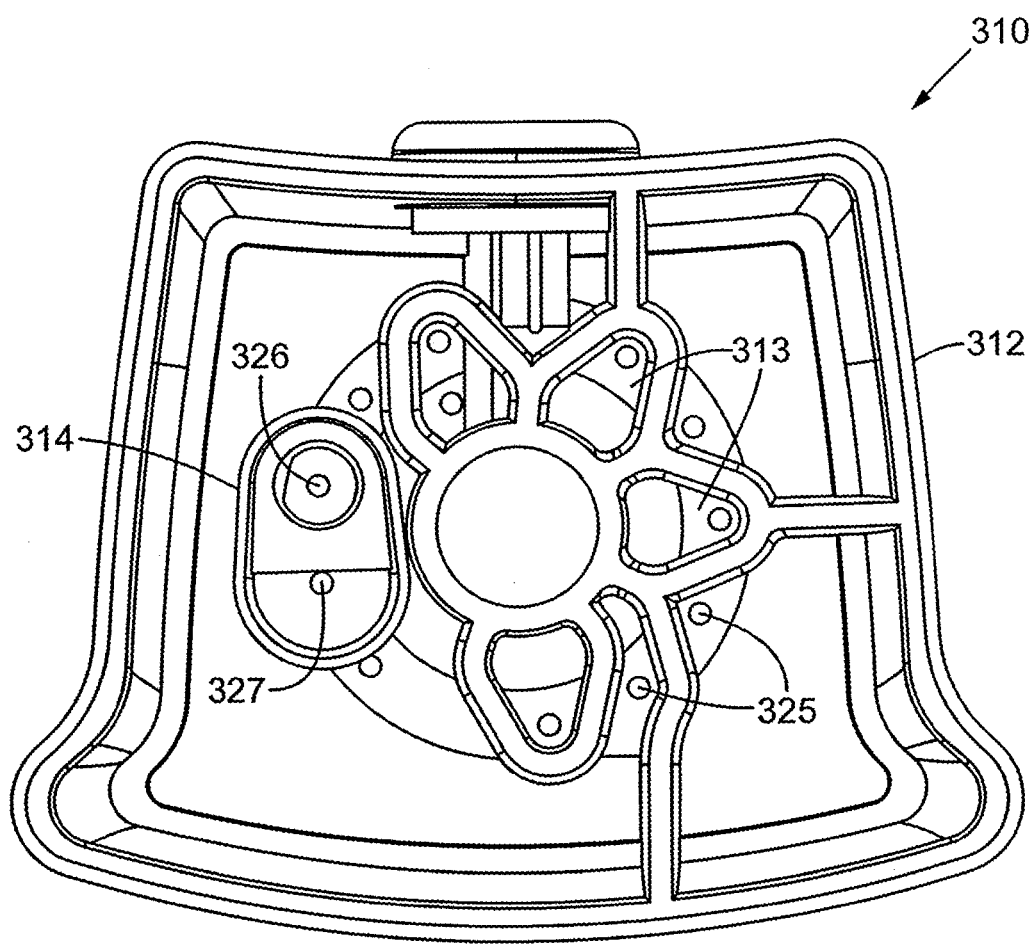
FIG. 16 is a top plan view of a fluid control and processing system including a processing chamber according to another embodiment of the present invention.

FIG. 16 shows a fluid control and processing system 310 including a housing 312 having a plurality of chambers 313 wherein one of the chambers is a processing chamber 314. The housing 312 includes a plurality of chamber ports 325 configured to communicate with a fluid control device such as a rotary fluid control valve similar to the rotary valve 16 in the system 10 of FIGS. 1-4. The valve has a fluid displacement region similar to the fluid displacement region 50 in the system 10. The chambers 313 may include the same chambers as in the embodiment of FIGS. 1-4 (i.e., sample chamber 60, waste chamber 64, wash chamber 66, lysis chamber 70, reagent chamber 78, and reaction vessel 18). The housing 312 also includes a fluid processing region or active region similar to the fluid processing region 30 of system 10 in FIGS. 1-4. In such a configuration, the chamber ports 325 will face the external port surface of the disk portion of a rotary fluid control valve The processing chamber 314 has a first port 326 and a second port 327. In one example, the first port 326 may be an inlet port for taking in fluid, and the second port 327 may be an outlet port for discharging fluid from the processing chamber 314. The processing chamber 314 typically is integrally formed or built into the main body of the housing 312, so that the inlet and outlet ports of the processing chamber are two of the chamber ports. Alternatively, the processing chamber 314 may be formed as a separate member that can be inserted into the main body of the housing 312, the inserted member having inlet and outlet ports that align with two of the chamber ports.

The processing chamber 314 may contain a processing chamber material, such as an enrichment material or medium or a depletion material or medium. An enrichment material captures a target such as an analyte from the fluid that passes through the processing chamber 314. A depletion material traps or retains unwanted material from the fluid that passes through the processing chamber 314. The enrichment or depletion material may comprise one or more solid phase materials. In general, the solid phase materials may include beads, fibers, membranes, filter paper, glass wool, polymers, and gels.

For example, enrichment materials may include chromatographic materials, more particularly absorptive phase materials, such as reverse phase materials, ion-exchange materials, or affinity chromatographic materials in which a binding member is covalently bound to an insoluble matrix. For the affinity chromatographic materials, the binding member may be group specific (e.g., a lectin, enzyme cofactor, Protein A and the like) or substance specific (e.g., antibody or binding fragment thereof, antigen for a particular antibody of interest, oligonucleotide and the like). The insoluble matrix to which the binding member is bound may be particles, such as porous glass or polymeric beads, networks of glass strands or filaments, a plurality of narrow rods or capillaries, and the like. For example, the insoluble matrix may include beads functionalized with antibodies for capturing antigens or haptens for an immunoassay procedure.

Instead of coated particles or other insoluble matrices, one may employ a coated/impregnated membrane which provides for selective retention of the analyte comprising fraction of a fluid sample while allowing the remainder of the sample to flow through the membrane and out of the processing chamber. A variety of hydrophilic, hydrophobic, and ion-exchange membranes have been developed for solid phase extraction.

Another example of an enrichment material is a gel medium, which can be used to provide for a diversity of different sieving capabilities. The enrichment channel through the processing chamber 314 serves to enrich a particular analyte comprising fraction of a liquid sample. By varying the pore size of the media, employing two or more gel media of different porosity, and/or providing for a pore size gradient, one can ensure that the analyte comprising fraction of interest of the initial sample is retained in the gel medium.

Figure 17:
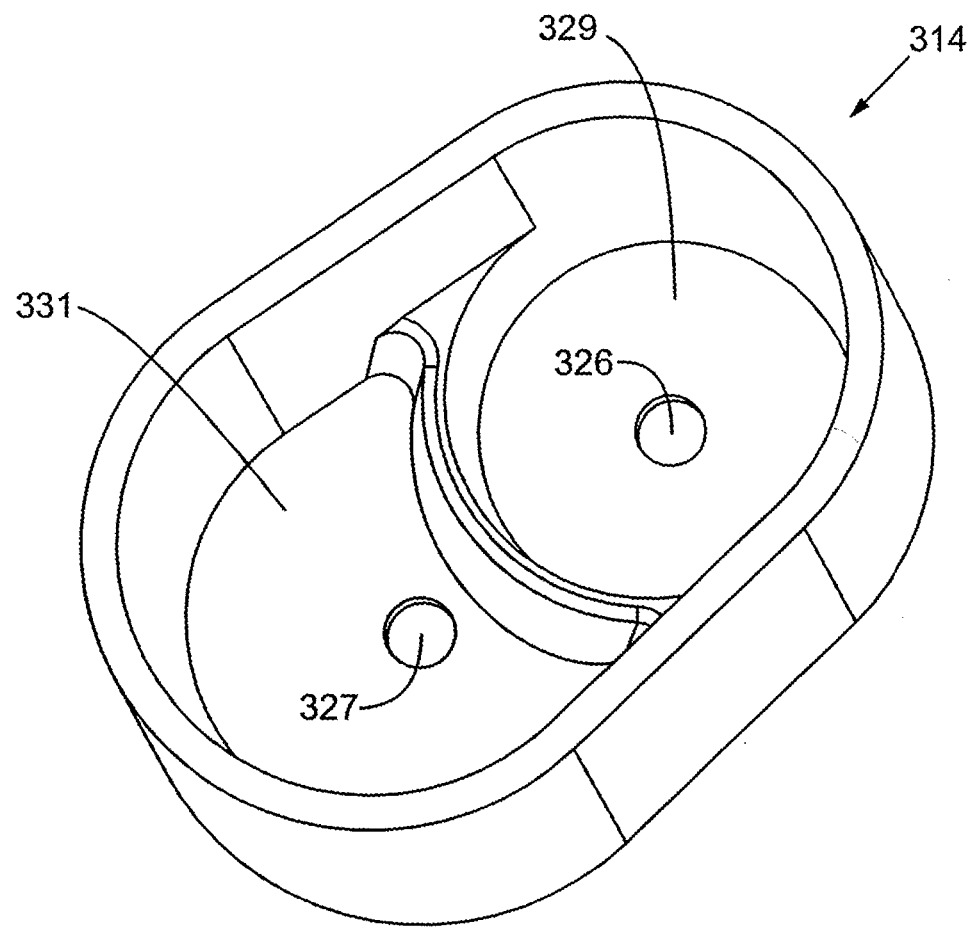
FIG. 17 is a perspective view of the processing chamber of FIG. 16.
Figure 18:
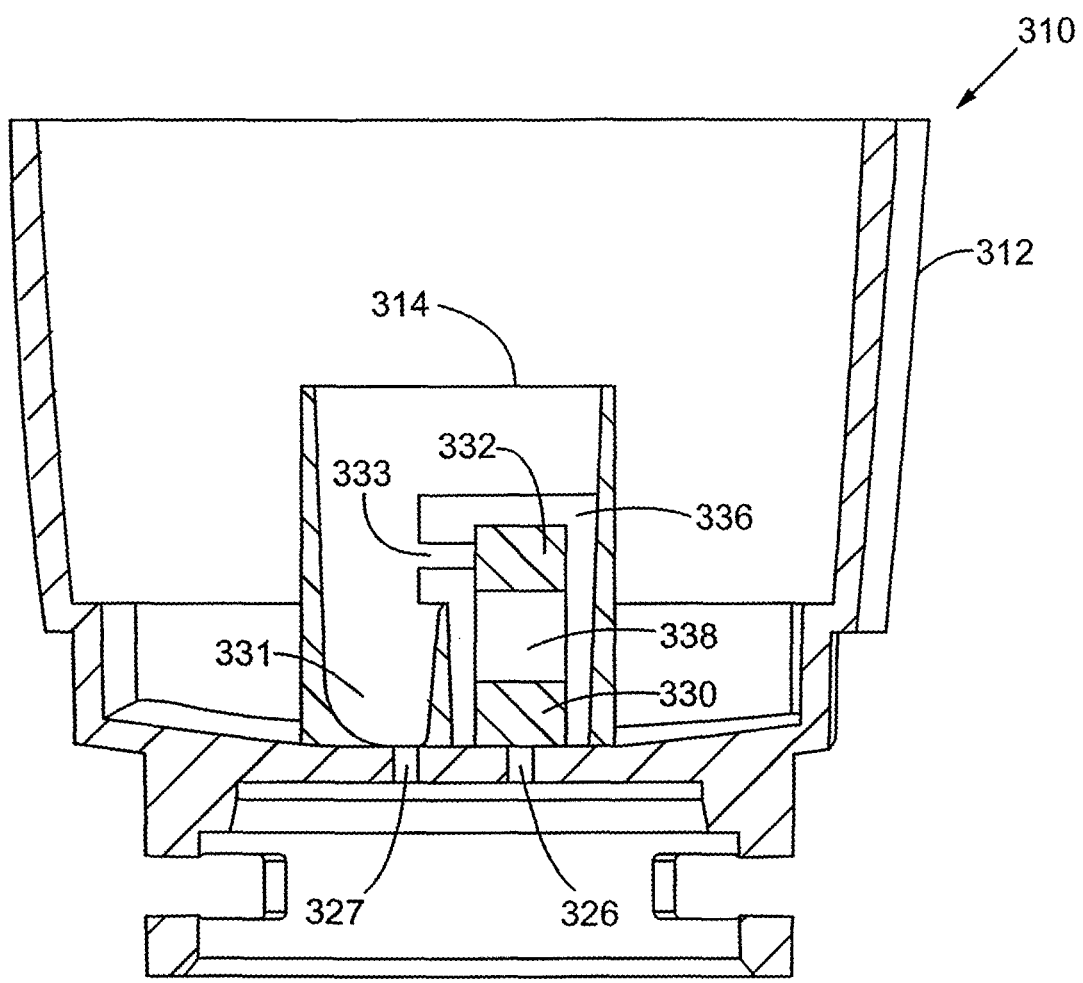
FIG. 18 is a partially cut-out, sectional view of the fluid control and processing system of FIG. 16.
Figure 19:
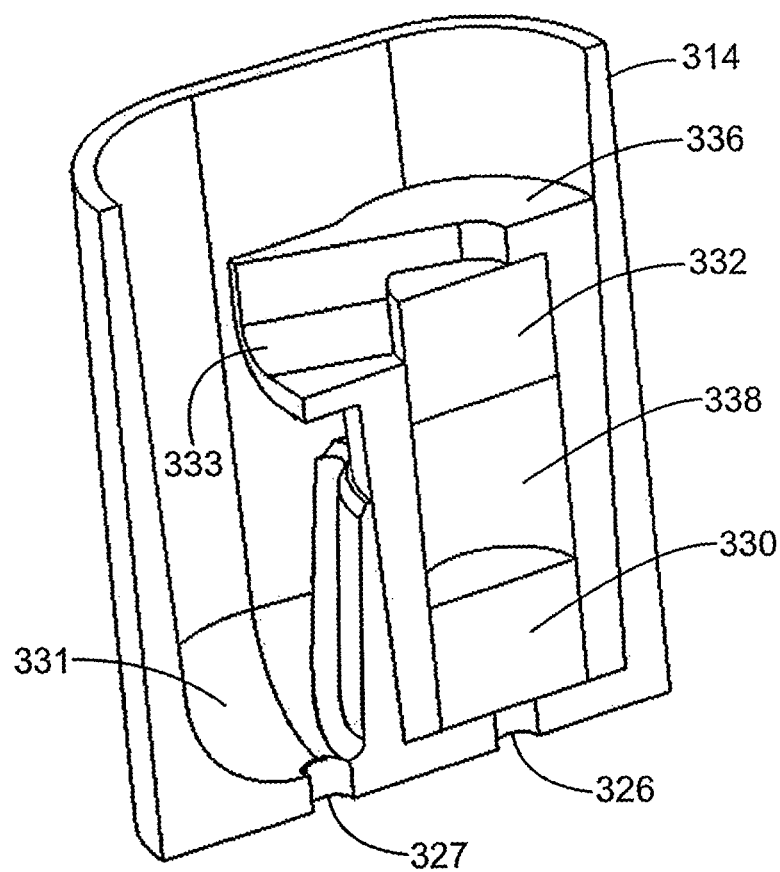
FIG. 19 is a sectional perspective view of the processing chamber of FIG. 16
Figure 20:
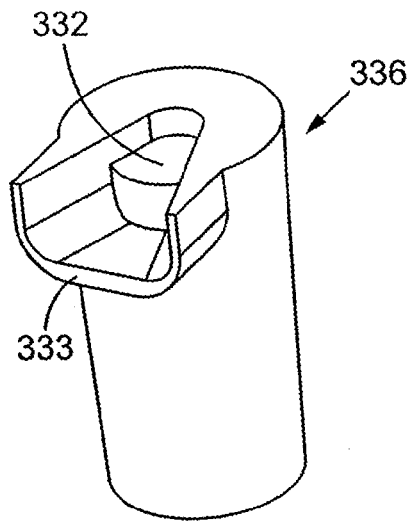
FIG. 20 is a perspective view of a retaining member of the processing chamber of FIG. 16.
Figure 21:
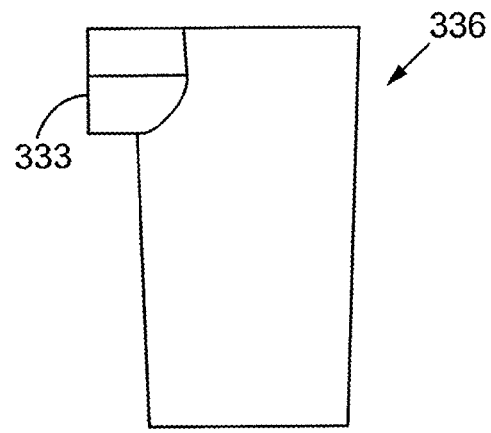
FIG. 21 is an elevational view of the retaining member of FIG. 20.
Figure 22:
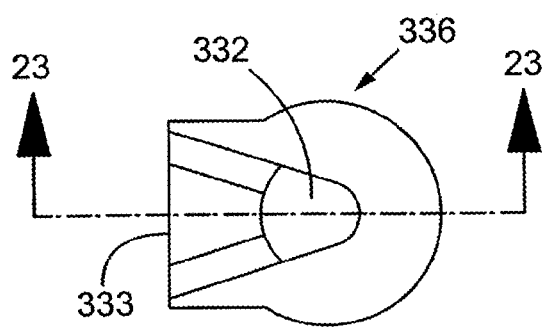
FIG. 22 is a top plan view of the retaining member of FIG. 20.
Figure 23:
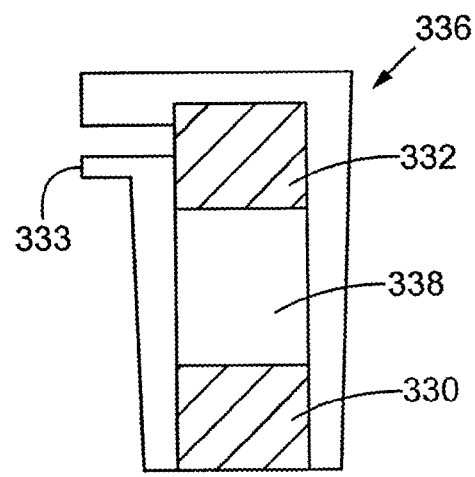
FIG. 23 is a cross-sectional view of the retaining member along 23-23 of FIG. 22.

For some enrichment materials or depletion materials, it may be necessary to employ a retention mechanism to keep the particular material in the processing chamber. Frits such as glass frits may be used to retain the material in the processing chamber. FIGS. 18-23 show two frits 330, 332 disposed inside the processing chamber 314. In the embodiment shown, the frits 330, 332 are held in place by a retaining structure or member 336. The retaining member 336 may be configured as a processing module or an insert that can be easily snapped into place in a receiving area of the processing chamber 314 and can be conveniently removed as desired. As shown in FIG. 17, in a specific embodiment, the processing chamber 314 includes a receiving area 329 for receiving a processing module containing an enrichment material or a depletion material. In other embodiments, the processing module may comprise a column containing a separation material or a structure containing a separation channel for capillary electrophoresis or isoelectric focusing. The processing chamber 314 has a collection area 331 for receiving fluid that has flowed through the processing module 336.

Referring to FIGS. 18-23, the processing module 336 preferably includes a spout 333 that directs the fluid into the collection area 331. The processing module includes a first frit 330 that is disposed adjacent the first port 326, and the second frit 332 is spaced from the first frit 330 to provide a space 338 for the enrichment material or depletion material. In one embodiment, the fluid enters the processing chamber 314 through the first port 326, passes through the first fit 330, the enrichment material or depletion material in the space 338, and the second frit 332, and then by gravity flows to the collection area 331 of the processing chamber above the second port 327 and exits the processing chamber 314 through the port 327. The space 338 serves as another fluid processing region.

In one example, a sample fluid is drawn from the sample chamber by rotating the valve to place the fluid displacement region in fluidic communication with the sample chamber via the first external port. This is illustrated for the system 10 of FIGS. 1-4 in FIGS. 9A and 9AA, which is generally the same as the system 310 of FIGS. 16-23 except for the additional processing chamber 314 in the system 310. The sample fluid bypasses the fluid processing region (region 30 in system 10), and enters the fluid displacement region (region 50 in system 10). The valve (valve 16 in system 10) is rotated to place the first external port in fluidic communication with the processing chamber 314. The sample fluid is driven from the fluid displacement region into the processing chamber 314 via the inlet port 326, bypassing the fluid processing region. As the fluid flows through the processing chamber 314 containing an enrichment material via the inlet port 326, for example, the analyte comprising sample fraction will be retained by the enrichment material such as a chromatographic material in the processing chamber 314. The remaining waste portion of the fluid is drawn out of the processing chamber 314 through the outlet port 327 and into the fluid displacement region of the valve by rotating the valve to place the first external port in fluidic communication with the outlet port 327 of the processing chamber 314. The valve is then rotated to place the first external port in fluidic communication with the waste chamber (chamber 64 in system 10), and the waste fluid is driven from the fluid displacement region into the waste chamber. An elution liquid may then flow through the enrichment material in the processing chamber 314 to release the enriched sample fraction from the enrichment material and carry it from the processing chamber 314 to another chamber or another region such as an active region. The elution liquid may be first drawn into the fluid displacement region of the valve from another chamber, and then driven from the fluid displacement region into the inlet port 326 of the processing chamber 314 by manipulating the rotary valve. The elution liquid and the released enriched sample fraction may be drawn from the processing chamber 314 via the outlet port 327, either into the fluid displacement region through the first external port (port 42 in system 10) bypassing the fluid processing region, or through the fluid processing region (region 30 in system 10) and into the fluid displacement region through the second external port (port 46 in system 10). The rotary valve may be further manipulated to transfer the fluid to other chambers or regions of the system 310.

In another example a depletion material is provided in the processing chamber 314 for trapping or removing unwanted material from a sample fluid. The valve can be used to transfer the sample fluid from the sample chamber to the processing chamber 314 as described above. As the fluid flows through the processing chamber 314 containing a depletion material via the inlet port 326, the unwanted materials such as cellular debris, contaminants, or amplification inhibitors are depleted from the fluid. The remaining fluid is drawn out of the processing chamber 314 through the outlet port 327 by rotating the valve to place the fluid displacement region in fluidic communication with the outlet port 327. The fluid may be drawn through the second external port (port 46 in system 10) first into the fluid processing region (region 30 in system 10) and then into the fluid displacement region of the valve. Alternatively, the fluid may be drawn through the first external port (port 42 in system 10) into the fluid displacement region bypassing the fluid processing region. The fluid may subsequently be driven from the fluid displacement region into another chamber or region of the system 310 by manipulating the rotary valve.

Instead of solid phase materials, the processing chamber 314 may house liquid phase materials such as, for example, ficoll, dextran, polyethylene glycol (PEG), sucrose, and the like.

By providing one or more processing chambers in the fluid processing system 310, the system 310 becomes more versatile, and is capable of performing additional steps of sample preparation other than those performed in the active region or processing region in the valve body (e.g., processing region 30 in FIG. 8), to achieve multi-staged filtration, consecutive functions, and the like in a single device. Moreover, the processing chamber may be fluidicly coupled with an external fluid volume to facilitate large volume processing. The processing chamber may also be fluidicly coupled with an external chamber that contains materials that are not desirable inside the main body 312 of the fluid processing system 310.

In general, the processing regions in the processing chambers (e.g., processing chamber 314 in FIG. 16) and in the valve body (e.g., processing region 30 in FIG. 8) may each contain enrichment materials or depletion materials. In some embodiments, each processing region may contain one or more such materials. For example, a filter (e.g., the filter or filter stack 27 in FIG. 8) or beads may be placed in a processing region to remove unwanted materials such as cellular debris from the sample or for accomplishing concentration of cells. The filter or beads may be used to bind specific targets such as particular molecules in the sample, or to remove specific targets such as proteins, inhibitors, or the like. In some embodiments, a processing region includes a filter and another solid phase material such as beads, fibers, or wool, for molecular isolation of molecular targets or molecular removal of molecular materials. In other embodiments, a processing region may include different types of beads such as magnetic beads, glass beads, polymeric beads, and the like. The beads can be used for cell capture, cell lysis, binding of analyte, binding of unwanted material, or the like. In some embodiments, a single type of beads may be used to perform two or more of the functions of cell capture, cell lysis, binding of analyte, and binding of unwanted material. For instance, cells can be adhered to the beads and lysed to release their nucleic acid content, and the lysate together with the released nucleic acid can be moved to a separate region or chamber for further processing, leaving behind the beads and their adherent cellular debris.

In another embodiment, a separation channel is provided for performing capillary electrophoresis (CE), isoelectric focusing (IEF), or the like. This may be done before or after nucleic acid amplification. The separation channel may be a separate member that is inserted into a chamber of the fluid processing system, may be formed as a microchannel in the housing of the system, or may be built into one of the chambers of the system.

Figure 24:
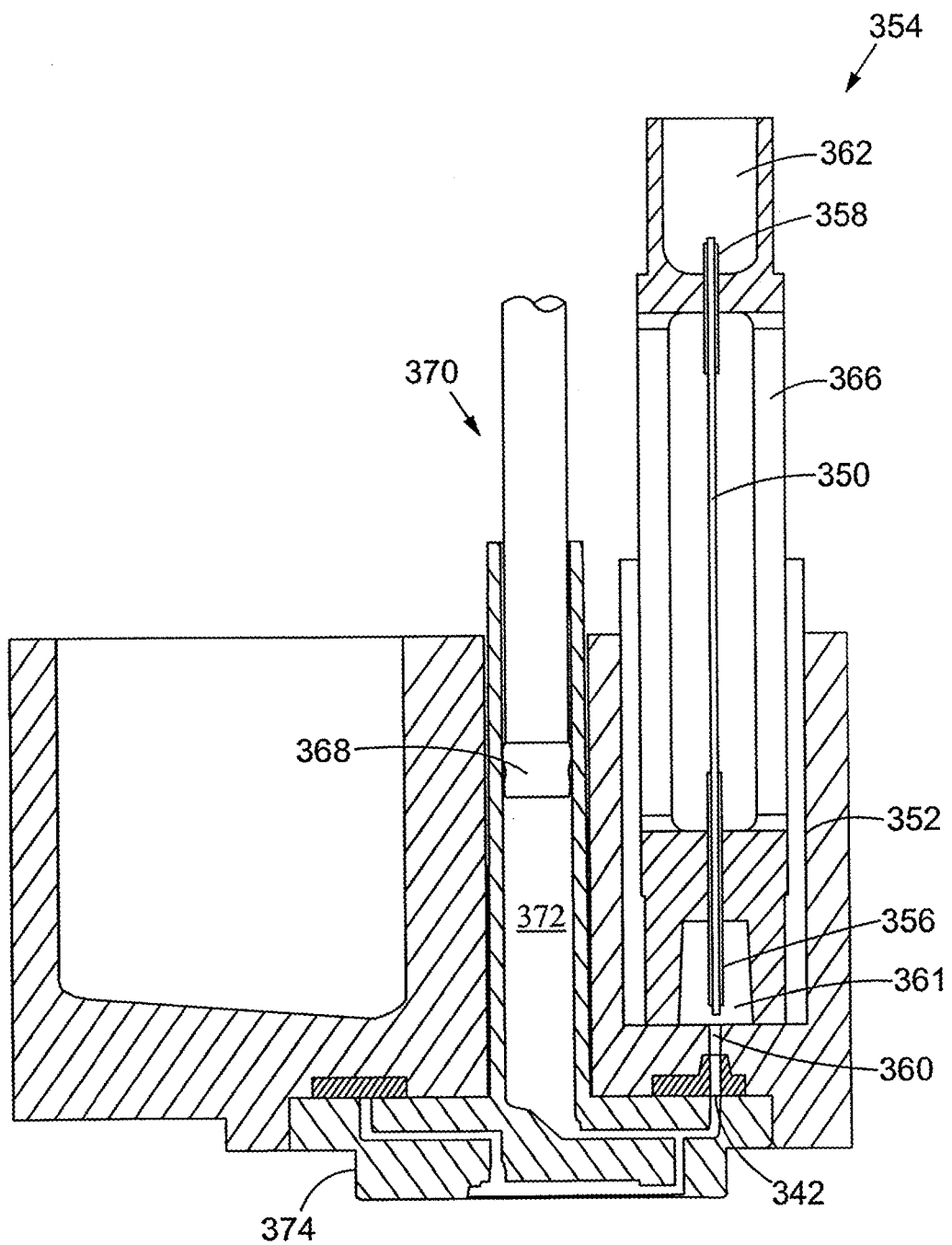
FIG. 24 is a sectional view of a fluid control and processing system including a separation channel according to another embodiment of the present invention.

FIG. 24 shows a separation channel or region 350 in the fluid control and processing system 354. The separation channel 350 is typically formed as a separate member that is assembled into the system 354 and may in some embodiments be disposed in a chamber 352. Alternatively, the separation channel 350 may be integrally formed or built into the system 354. The separation channel 350 may be a thin channel or a capillary coupled between at least two electrodes, which in the specific embodiment shown include two metal tubes 356, 358. The lower end of the channel 350 is fluidicly coupled to a lower reservoir 361 which is fluidically coupled to a chamber port or reservoir port 360, while the upper end of the channel 350 is fluidically coupled to a vented reservoir 362 provided in a support structure 366 for supporting the separation channel 350. The metal tubes 356, 358 serve as electrodes to receive electrical energy and apply an electric field to the fluid in the separation channel 350. Conductive wires in contact with the metal tubes 356, 358 may be molded into plastic and lead to respective contact areas on the external surface of the housing of the system 354. A voltage source may then be connected to the contact areas to apply a voltage difference between the contact areas and thus between the electrodes. Alternatively, electrodes may be provided as part of an external instrument for applying the electric field, and be dipped into reservoirs at the ends of the separation channel 350. The sample fluid is typically pumped by the piston 368 of the valve 370 from the fluid displacement region 372 through one of the external ports of the valve body (e.g., the external port 342) to the separation channel 350 via the reservoir port 360 and reservoir 361. A sample plug is injected into the separation channel 350, and the remaining portion of the sample fluid in the reservoir 361 may then be drawn via the chamber port 360 into the fluid displacement region 372 of the valve 370 by the piston 368. The reservoir 362 may be used to introduce buffer, elution solvent, reagent, rinse and wash solutions, or the like into the electrophoretic flow path of the separation channel 350.

Entities in the sample plug, such as molecules, particles, cells, and the like are moved through a medium contained in the separation channel 350 under the influence of the applied electric field. Depending on the nature of the entities (e.g., whether they carry an electrical charge), as well as the surface chemistry of the electrophoretic chamber in which the electrophoresis is carried out, the entities may be moved through the medium under the direct influence of the applied electric field or as a result of bulk fluid flow through the pathway resulting from the application of the electric field such as an electroosmotic flow. As the sample plug separates into species bands in the separation channel 350, the bands are detected, for instance, optically by a single point detector disposed at a fixed location or by a scanning detector that scans along the length of the channel 350. To facilitate optical detection, a portion of the housing may be optically transmissive or transparent. Alternatively, the detector may be inserted into the housing and placed adjacent the channel 350 (e.g., in a chamber which houses the channel 350).

Typically, separation is performed after amplification, for instance, using the method as described above in FIGS. 9A-9LL. In one example, an amplified product (e.g., nucleic acid amplified by PCR) is introduced as the sample into the reservoir 361. The separation channel 350 is prefilled with a separation material such a gel or buffer. A voltage is applied via the electrodes 356, 358 to inject a sample plug from the reservoir 361. The rest of the sample is then removed from the reservoir 361. Next, a buffer such as an electrolyte solution is introduced into the reservoir 361. A voltage difference is applied between the electrodes 356, 358 to form an electric field that induces flow of a sample plug through the separation channel 350 and separates the sample plug therein into species bands, which are detected using, for instance, a single-point optical detector or a scanning detector.

Figure 25:
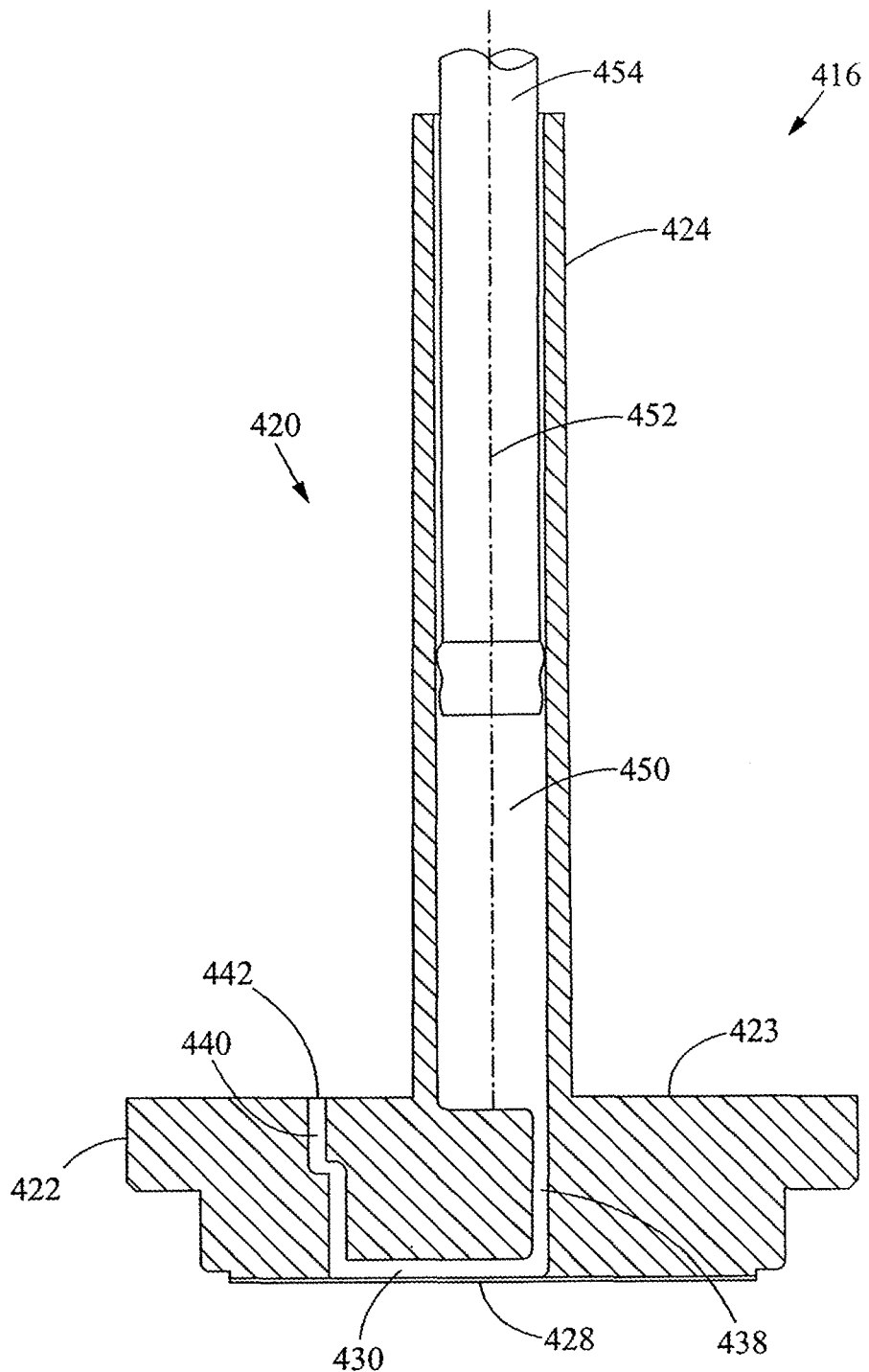
FIG. 25 is a cross-sectional view of a fluid control apparatus in a fluid control and processing system according to another embodiment of the present invention.

FIG. 25 shows the valve 416 of another system 410 which has a housing with a plurality of chambers similar to the system 10 of FIGS. 1-4, except that the valve 416 has only one external port 442. The valve 416 includes a valve body 420 having a disk portion 422 and a tubular portion 424. The disk portion 422 has a generally planar external port surface 423. The valve 416 is rotatable relative to the housing 412 of the system 410 (see FIGS. 26A and 26AA). The housing 412 includes a plurality of chamber ports facing the external port surface 423 of the disk portion 422 of the valve 416 to permit fluidic communication between the chambers of the housing 412 and the valve 416. The disk portion 422 includes a fluid processing region 430, a first flow channel 440 extending between the external port 442 and the fluid processing region 430, and a second flow channel 438 extending between the fluid processing region 430 and a fluid displacement region 450 in the tubular portion 424 of the valve 416. The fluid processing region 430 is in continuous fluidic communication with the fluid displacement region 450. An outer cover 428 is placed over the fluid processing region 430. The fluid processing region 430 may be used to subject a fluid flowing therethrough to various acoustical, optical, thermal, electrical, mechanical, or chemical processing.

As shown in FIG. 25, a fluid displacement member in the form of a plunger or piston 454 is movably disposed in the displacement region 450 of the tubular portion 424 to move up and down along the axis 452. When the piston 454 moves upward, it expands the volume of the displacement region 450 to produce a suction for drawing fluid into the region 450. When the piston 454 moves downward, it decreases the volume of the displacement region 450 to drive fluid out of the region 450. As the rotary valve 416 is rotated around its axis 452 relative to the housing 412, the external port 442 may be fluidicly coupled with one of the chambers or reaction vessel in the housing 412. Depending on the action of the piston 454, the external port 442 is either an inlet port or an outlet port.

Figure 26B:
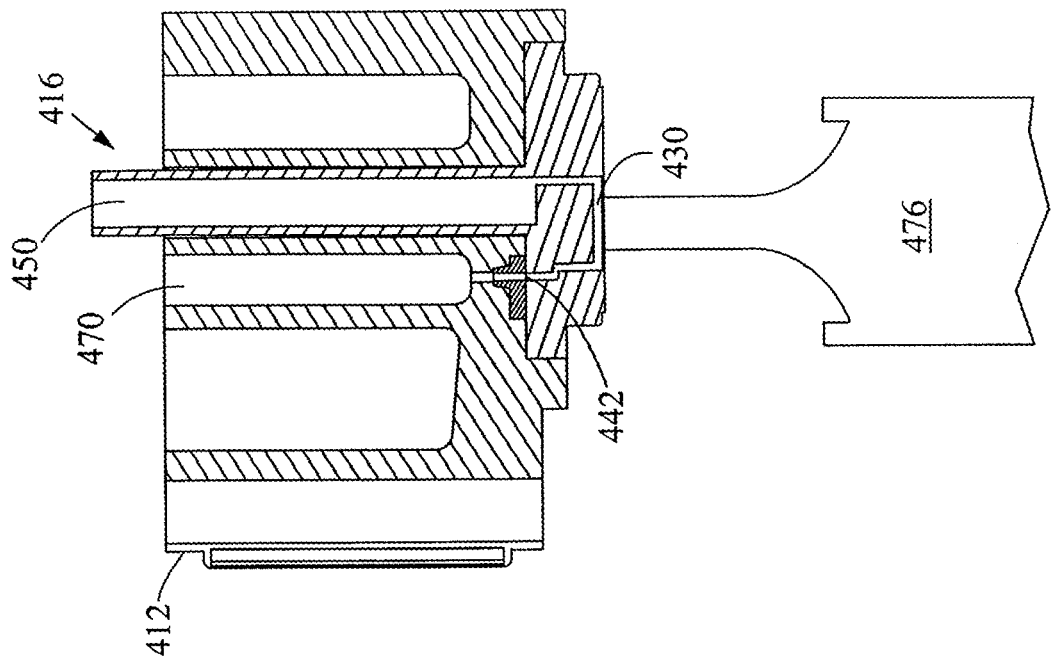
Figure 26B:
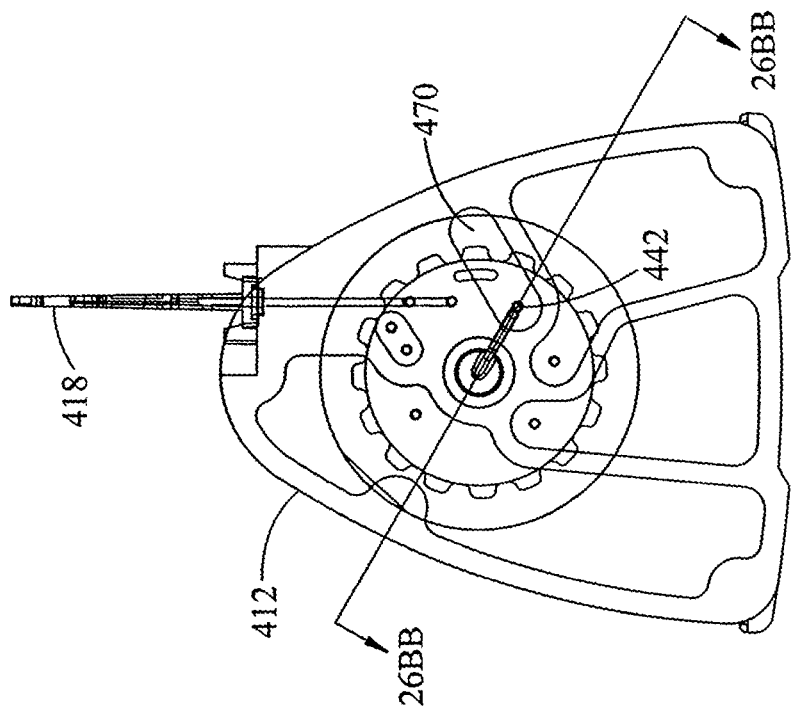

To demonstrate the fluid metering and distribution function of the valve 416, FIGS. 26A-26EE illustrate the operation of the valve 416 for a specific protocol. In FIGS. 26A and 26AA, the external port 442 is placed in fluidic communication with a sample chamber 460 by rotating the valve 416, and the piston 454 is pulled upward to draw a fluid sample from the sample chamber 460 through the first flow channel 440, the fluid processing region 430, and the second flow channel 438 and into the fluid displacement region 450. For simplicity, the piston 454 is not shown in FIGS. 26A-26EE.

As shown in FIGS. 26B and 26BB, the valve 416 is then rotated to place the external port 442 in fluidic communication with a storage chamber 470 which contains a lysing fluid (e.g., a lysing reagent or buffer). The piston 454 is pushed downward to transfer the fluid sample from the fluid displacement region 450 to the storage chamber 470. The piston 454 is then pulled upward to draw the fluid sample and lysing fluid from the storage chamber 470 to the fluid displacement region 450. The lysing fluid mixes with the sample and effects lysis of cell or viruses in the sample. Additional energy may be applied to the processing region 430 to assist the lysing process. For instance, a sonic member 476 such as an ultrasonic horn may be placed in contact with the outer cover 428 to transmit ultrasonic energy into the processing region 430 to facilitate lysing of cells or viruses of the fluid sample as the fluid flows from the fluid displacement region 450 to the storage chamber 470 and/or from the storage chamber 470 back to the fluid displacement region 450. The outer cover 428 in one preferred embodiment is an interface wall which is dome-shaped or includes stiffening ribs.

Figure 26C:
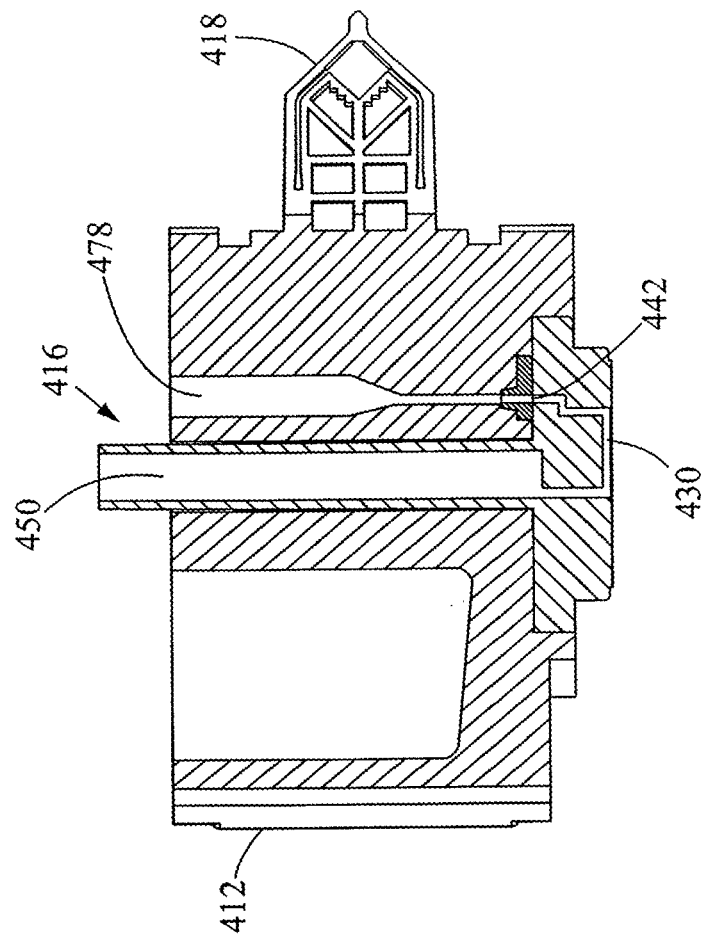
Figure 26C:
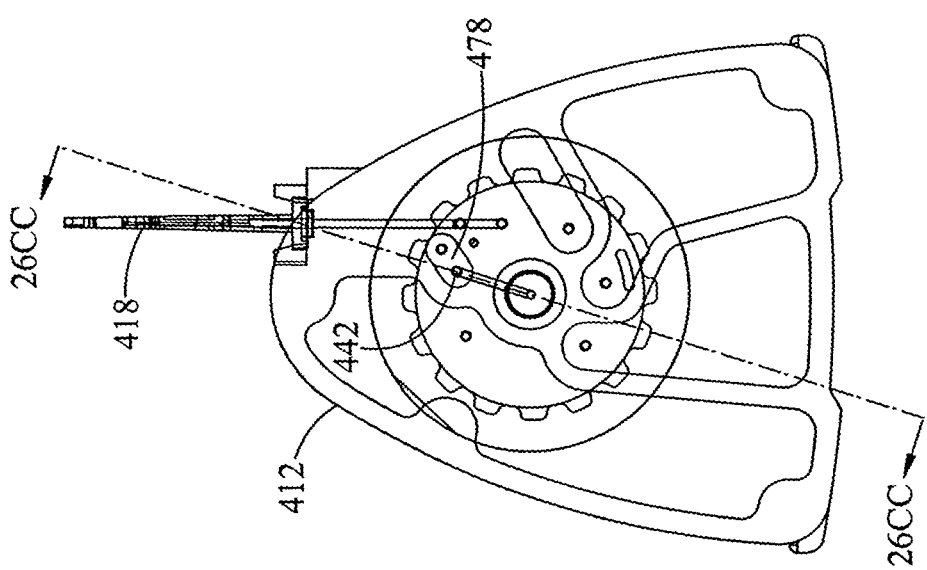

In FIGS. 26C and 26CC, the valve 416 is rotated to place the external port 442 in fluidic communication with a reagent chamber 478, and the piston 454 is pushed downward to force the lysate to flow from the fluid processing region 430 to the reagent chamber 478. The reagent chamber 478 typically contains reagents (e.g., PCR reagents and fluorescent probes) to be mixed with the fluid sample. The fluids are then mixed in the reagent chamber 478 by toggling the mixture between the fluid displacement region 450 and the reagent chamber 478 as the piston 454 is moved up and down.

In FIGS. 26D, 26DD, and 26D'D', the valve 416 is rotated to place the external port 442 in fluidic communication with a first branch 484 coupled to the reaction vessel 418, while the second branch 486 which is coupled to the reaction vessel 418 is placed in fluidic communication with the crossover groove 456. The first branch 484 and second branch 486 are disposed at different radii from the axis 452 of the valve 416, with the first branch 484 having a common radius with the external port 442 and the second branch 486 having a common radius with the crossover groove 456. The crossover groove 456 is also in fluidic communication with the reagent chamber 478 (FIG. 26D), and serves to bridge the gap between the reagent chamber 478 and the second branch 486 to provide crossover flow therebetween. The external port is disposed within a range of external port radii from the axis and the crossover groove is disposed within a range of crossover groove radii from the axis, where the range of external port radii and the range of crossover groove radii are non-overlapping. Placing the crossover groove 456 at a different radius from the radius of the external port 442 is advantageous because it avoids cross-contamination of the crossover groove 456 by contaminants that may be present in the area near the surfaces between the valve 416 and the housing 412 at the radius of the external port 442 as a result of rotational movement of the valve 416.

To fill the reaction vessel 418, the piston 454 is pulled upward to draw the mixture in the reagent chamber 478 through the crossover groove 456 and the second branch 486 into the reaction vessel 418. In such an arrangement, the reaction vessel 418 is the aspiration chamber or referred to as the first chamber, and the reagent chamber 478 is the source chamber or referred to as the second chamber. The valve 416 is then rotated to place the external port in fluidic communication with the first branch 484, as shown in FIGS. 26E and 26EE. The piston 454 is pushed downward to pressurize the mixture inside the reaction vessel 418. The reaction vessel 418 may be inserted into a thermal reaction chamber for performing nucleic acid amplification and/or detection. The two branches 484, 486 allow filling and evacuation of the reaction chamber of the reaction vessel 418.

The fluid control and processing system 410 of FIGS. 26-26EE is modified from the system 10 of FIGS. 1-9LL to provide only one external port. Similarly, the valve 100 of FIGS. 10-12 may also be modified to provide only one external port by removing one of the two external ports 111, 112 and reconfiguring the fluid channels 130-138 and branches 140, 142 between the valve 100 and the various chambers and reaction vessel 104.

The scope of the invention should, therefore, be determined not with reference to the above description, but instead should be determined with reference to the appended claims along with their full scope of equivalents.

What is claimed is:

1. A fluid control and processing system comprising:
   a housing having a plurality of chambers and at least one separation channel; and
   a valve body including a fluid processing region continuously coupled fluidicly with a fluid displacement region, the fluid displacement region including or being connected to a means that depressurizes the fluid displacement region to draw fluid into the fluid displacement region and pressurizes the fluid displacement region to expel fluid from the fluid displacement region, the valve body including at least one external port, the fluid processing region being fluidicly coupled with the at least one external port, the fluid displacement region being fluidicly coupled with at least one external port of the valve body, and the valve body being adjustable with respect to the housing to allow the at least one external port to be placed selectively in fluidic communication with the plurality of chambers and with the at least one separation channel.

2. The system of claim 1, further comprising a plurality of electrodes coupled to the housing to apply an electric field across at least a portion of the separation channel.

3. The system of claim 2, wherein the electrodes comprise a pair of metal tubes at the two opposite ends of the separation channel.

4. The system of claim 1, further comprising reservoirs fluidicly coupled to opposite ends of the separation channel, and a reservoir port fluidicly coupled to one of the reservoirs for communicating with the at least one external port of the valve body.

5. The system of claim 1, wherein at least one of the chambers is a reagent chamber containing dried or lyophilized reagents.

6. A method for controlling fluid flow between the valve body, the plurality of chambers, and the at least one separation channel of the system of claim 1, the method comprising:
adjusting the valve body with respect to the plurality of chambers and the at least one separation channel to place the at least one external port selectively in fluidic communication with the plurality of chambers and the separation channel.

7. The method of claim 6, further comprising applying an electric field across at least a portion of the separation channel.

8. The method of claim 6, wherein the external port is placed in fluidic communication with the separation channel via a reservoir fluidicly coupled to one end of the separation channel, the reservoir having a reservoir port for communicating with the at least one external port of the valve body.

9. The method of claim 6, further comprising optically detecting species bands in the separation channel.

* * * * *